United States Patent
Hasan et al.

(10) Patent No.: US 12,089,930 B2
(45) Date of Patent: Sep. 17, 2024

(54) METHOD AND APPARATUS FOR NON-INVASIVE HEMOGLOBIN LEVEL PREDICTION

(71) Applicant: Marquette University, Milwaukee, WI (US)

(72) Inventors: Md Kamrul Hasan, Milwaukee, WI (US); Sheikh Iqbal Ahamed, Fox Point, WI (US); Richard R. Love, Madison, WI (US)

(73) Assignee: Marquette University, Milwaukee, WI (US)

( * ) Notice: Subject to any disclaimer, the term of this patent is extended or adjusted under 35 U.S.C. 154(b) by 946 days.

(21) Appl. No.: 16/978,129

(22) PCT Filed: Mar. 5, 2019

(86) PCT No.: PCT/US2019/020675
§ 371 (c)(1),
(2) Date: Sep. 3, 2020

(87) PCT Pub. No.: WO2019/173283
PCT Pub. Date: Sep. 12, 2019

(65) Prior Publication Data
US 2021/0007648 A1     Jan. 14, 2021

Related U.S. Application Data

(60) Provisional application No. 62/638,630, filed on Mar. 5, 2018.

(51) Int. Cl.
*A61B 5/1455* (2006.01)
*A61B 5/00* (2006.01)

(52) U.S. Cl.
CPC ........ *A61B 5/14552* (2013.01); *A61B 5/6826* (2013.01); *A61B 5/6898* (2013.01); *A61B 2576/02* (2013.01)

(58) Field of Classification Search
CPC .............. A61B 5/1455; A61B 5/14551; A61B 5/14552; A61B 5/6826; A61B 5/6898; A61B 2576/02
See application file for complete search history.

(56) References Cited

U.S. PATENT DOCUMENTS

| | | |
|---|---|---|
| 4,485,820 A | 12/1984 | Flower |
| 5,277,181 A | 1/1994 | Mendelson et al. |

(Continued)

FOREIGN PATENT DOCUMENTS

| | | |
|---|---|---|
| AU | 2013237667 A1 | 10/2013 |
| AU | 2013201634 B2 | 5/2015 |

(Continued)

OTHER PUBLICATIONS

Raikhel, Accuracy of noninvasive and invasive point-of-care total blood hemoglobin measurement in an outpatient setting, Postgraduate Medicine, 2012, 124(4):250-255.

(Continued)

*Primary Examiner* — Eric F Winakur
(74) *Attorney, Agent, or Firm* — Quarles & Brady LLP

(57) ABSTRACT

An image-based hemoglobin estimation tool for measuring hemoglobin can be embedded in hand held devices such as smartphones, and similar known and to be developed technology. The hand-held device acquires video data of a finger illuminated from the dorsal surface by a first near infrared light responsive to hemoglobin and a second near infrared light near responsive to plasma. The acquired video is segmented into frames and processed to produce a Photoplethysmography (PPG) waveform. The features of the PPG waveform can then be identified, and the waveform and corresponding features evaluated by a predictive hemoglobin model. The predictive hemoglobin model can be provided at a remote computer, enabling non-invasive hemoglobin analysis from point of care locations. Near infrared (Continued)

lights of 850 nm and 1070 nm are particularly effective in the process.

19 Claims, 9 Drawing Sheets

(56) References Cited

U.S. PATENT DOCUMENTS

| | | |
|---|---|---|
| 5,365,066 A | 11/1994 | Krueger, Jr. et al. |
| 5,385,143 A | 1/1995 | Aoyagi |
| 5,424,545 A | 6/1995 | Block et al. |
| 5,634,461 A | 6/1997 | Faithfull et al. |
| 5,701,902 A | 12/1997 | Vari et al. |
| 5,717,605 A | 2/1998 | Komiya et al. |
| 5,788,647 A | 8/1998 | Eggers |
| 5,810,723 A | 9/1998 | Aldrich |
| 5,813,987 A | 9/1998 | Modell et al. |
| 5,885,621 A | 3/1999 | Head et al. |
| 5,928,155 A | 7/1999 | Eggers et al. |
| 5,978,691 A | 11/1999 | Mills |
| 6,007,996 A | 12/1999 | McNamara et al. |
| 6,028,311 A * | 2/2000 | Sodickson ............ A61B 5/1455 356/405 |
| 6,033,862 A | 3/2000 | Matsuda et al. |
| 6,081,612 A | 6/2000 | Gutkowicz-Krusin et al. |
| 6,088,099 A | 7/2000 | Cabib et al. |
| 6,165,734 A | 12/2000 | Garini et al. |
| 6,208,749 B1 | 3/2001 | Gutkowicz-Krusin et al. |
| 6,276,798 B1 | 8/2001 | Gil et al. |
| 6,402,697 B1 | 6/2002 | Calkins et al. |
| 6,556,853 B1 | 4/2003 | Cabib et al. |
| 6,615,064 B1 | 9/2003 | Aldrich |
| 6,648,820 B1 | 11/2003 | Sarel |
| 6,743,172 B1 | 6/2004 | Blike |
| 6,905,827 B2 | 6/2005 | Wohlgemuth et al. |
| 6,936,254 B2 | 8/2005 | Baker et al. |
| 7,026,121 B1 | 4/2006 | Wohlgemuth et al. |
| 7,058,515 B1 | 6/2006 | Selifonov et al. |
| 7,187,790 B2 | 3/2007 | Sabol et al. |
| 7,189,507 B2 | 3/2007 | Mack et al. |
| 7,194,301 B2 | 3/2007 | Jenkins et al. |
| RE39,672 E | 6/2007 | Shehada et al. |
| 7,270,970 B2 | 9/2007 | Anderson et al. |
| 7,365,858 B2 | 4/2008 | Fang-Yen et al. |
| 7,394,919 B2 | 7/2008 | Rowe et al. |
| 7,490,085 B2 | 2/2009 | Walker et al. |
| 7,539,330 B2 | 5/2009 | Rowe |
| 7,545,963 B2 | 6/2009 | Rowe |
| 7,659,077 B2 | 2/2010 | Lund et al. |
| 7,684,934 B2 | 3/2010 | Shvartsburg et al. |
| 7,709,461 B2 | 5/2010 | Liu et al. |
| 7,711,662 B2 | 5/2010 | Buscema |
| 7,785,797 B2 | 8/2010 | Wohlgemuth et al. |
| 7,968,088 B2 | 6/2011 | Honmou et al. |
| 8,138,265 B2 | 3/2012 | Calabro et al. |
| 8,207,262 B2 | 6/2012 | Calabro et al. |
| 8,229,185 B2 | 7/2012 | Ennis et al. |
| 8,252,743 B2 | 8/2012 | Guyon et al. |
| 8,257,696 B2 | 9/2012 | Steindler et al. |
| 8,283,122 B2 | 10/2012 | Khan et al. |
| 8,285,366 B2 | 10/2012 | Hyde et al. |
| 8,285,367 B2 | 10/2012 | Hyde et al. |
| 8,306,607 B1 | 11/2012 | Levi et al. |
| 8,335,652 B2 | 12/2012 | Soykan et al. |
| 8,399,525 B2 | 3/2013 | Lockhart |
| 8,425,444 B2 | 4/2013 | Keenan et al. |
| 8,435,167 B2 | 5/2013 | Oohashi et al. |
| 8,457,705 B2 | 6/2013 | Shoureshi et al. |
| 8,478,389 B1 | 7/2013 | Brockway et al. |
| 8,500,636 B2 | 8/2013 | Tran |
| 8,548,549 B2 | 10/2013 | Schurman et al. |
| 8,583,565 B2 | 11/2013 | Shoureshi et al. |
| 8,585,627 B2 | 11/2013 | Dacey, Jr. et al. |
| 8,606,592 B2 | 12/2013 | Hyde et al. |
| 8,684,900 B2 | 4/2014 | Tran |
| 8,684,922 B2 | 4/2014 | Tran |
| 8,706,518 B2 | 4/2014 | Hyde et al. |
| 8,708,903 B2 | 4/2014 | Tran |
| 8,738,395 B2 | 5/2014 | Hyde et al. |
| 8,743,354 B2 | 6/2014 | Barrett et al. |
| 8,814,923 B2 | 8/2014 | Nissiläet al. |
| 8,870,813 B2 | 10/2014 | Ferren et al. |
| 8,913,800 B2 | 12/2014 | Rowe |
| 8,928,671 B2 | 1/2015 | Adler et al. |
| 8,928,877 B2 | 1/2015 | Lim et al. |
| 8,968,195 B2 | 3/2015 | Tran |
| 9,005,263 B2 | 4/2015 | Boyden et al. |
| 9,028,405 B2 | 5/2015 | Tran |
| 9,037,217 B1 | 5/2015 | Peyman |
| 9,060,722 B2 | 6/2015 | Teixeira |
| 9,064,036 B2 | 6/2015 | Hyde et al. |
| 9,091,676 B2 | 7/2015 | Rule et al. |
| 9,106,038 B2 | 8/2015 | Telfort et al. |
| 9,131,844 B2 | 9/2015 | Heanue et al. |
| 9,132,145 B2 | 9/2015 | Lee-Huang et al. |
| 9,159,223 B2 | 10/2015 | Proud |
| 9,298,985 B2 | 3/2016 | Krueger |
| 9,332,917 B2 | 5/2016 | Zhang |
| 9,340,772 B2 | 5/2016 | Bhatia et al. |
| 9,345,404 B2 | 5/2016 | Proud |
| 9,361,572 B2 | 6/2016 | Proud et al. |
| 9,392,943 B2 | 7/2016 | Reinisch |
| 9,402,546 B2 | 8/2016 | Segman |
| 9,436,903 B2 | 9/2016 | Proud et al. |
| 9,445,651 B2 | 9/2016 | Proud et al. |
| 9,456,776 B2 | 10/2016 | Ando |
| 9,462,856 B2 | 10/2016 | Proud et al. |
| 9,501,624 B2 | 11/2016 | Vishnubhatla et al. |
| 9,510,765 B2 | 12/2016 | Greder |
| 9,510,974 B1 | 12/2016 | Peyman |
| 9,528,817 B2 | 12/2016 | Fang-Yen et al. |
| 9,553,486 B2 | 1/2017 | Proud et al. |
| 9,554,742 B2 | 1/2017 | Lim et al. |
| 9,560,967 B2 | 2/2017 | Hyde et al. |
| 9,569,719 B2 | 2/2017 | Proud et al. |
| 9,569,720 B2 | 2/2017 | Proud et al. |
| 9,576,236 B2 | 2/2017 | Proud et al. |
| 9,582,748 B2 | 2/2017 | Proud et al. |
| 9,582,749 B2 | 2/2017 | Proud et al. |
| 9,619,883 B2 | 4/2017 | Yudovsky |
| 9,626,650 B2 | 4/2017 | Hwang et al. |
| 9,655,558 B2 | 5/2017 | Proud et al. |
| 9,662,015 B2 | 5/2017 | Proud et al. |
| 9,687,670 B2 | 6/2017 | Dacey, Jr. et al. |
| 9,704,209 B2 | 7/2017 | Proud et al. |
| 9,706,952 B2 | 7/2017 | Zhang |
| 9,714,900 B2 | 7/2017 | Haider et al. |
| 9,724,489 B2 | 8/2017 | Barbour et al. |
| 9,743,837 B2 | 8/2017 | Ando |
| 9,764,162 B1 | 9/2017 | Willcut et al. |
| 9,770,189 B2 | 9/2017 | Hyde et al. |
| 9,801,542 B2 | 10/2017 | Tran et al. |
| 9,814,425 B2 | 11/2017 | Tran |
| 9,820,657 B2 | 11/2017 | Tran |
| 9,841,415 B2 | 12/2017 | Kim et al. |
| 9,858,540 B2 | 1/2018 | Firminger et al. |
| 9,886,729 B2 | 2/2018 | Firminger et al. |
| 9,892,435 B2 | 2/2018 | Firminger et al. |
| 9,911,165 B2 | 3/2018 | Firminger et al. |
| 9,931,171 B1 | 4/2018 | Peyman |
| 9,946,344 B2 | 4/2018 | Ayaz et al. |
| 9,956,393 B2 | 5/2018 | Perez et al. |
| 9,968,264 B2 | 5/2018 | Tzvieli et al. |
| 9,993,197 B2 | 6/2018 | Proud |
| 9,994,228 B2 | 6/2018 | Krueger |
| 9,999,351 B2 | 6/2018 | Proud |
| 10,045,726 B2 | 8/2018 | Tzvieli et al. |
| 10,045,737 B2 | 8/2018 | Tzvieli et al. |
| 10,052,016 B2 | 8/2018 | Ehlers et al. |
| 10,064,559 B2 | 9/2018 | Tzvieli et al. |
| 10,076,250 B2 | 9/2018 | Tzvieli et al. |
| 10,076,270 B2 | 9/2018 | Tzvieli et al. |
| 10,085,642 B2 | 10/2018 | Frederick et al. |
| 10,085,643 B2 | 10/2018 | Bandic et al. |

(56) References Cited

U.S. PATENT DOCUMENTS

| | | |
|---|---|---|
| 10,085,685 B2 | 10/2018 | Tzvieli et al. |
| 10,094,649 B2 | 10/2018 | Bagherinia |
| 10,111,923 B2 | 10/2018 | Ma et al. |
| 10,117,617 B2 | 11/2018 | Cantu et al. |
| 10,118,006 B2 | 11/2018 | Davidson et al. |
| 10,136,852 B2 | 11/2018 | Tzvieli et al. |
| 10,136,856 B2 | 11/2018 | Tzvieli et al. |
| 10,216,981 B2 | 2/2019 | Tzvieli et al. |
| 10,219,705 B2 | 3/2019 | Addison et al. |
| 10,261,071 B2 | 4/2019 | Hall et al. |
| 10,272,029 B2 | 4/2019 | Ahlfors |
| 10,299,717 B2 | 5/2019 | Tzvieli et al. |
| 10,335,302 B2 | 7/2019 | Perez et al. |
| 10,351,620 B2 | 7/2019 | Rodriguez et al. |
| 10,354,051 B2 | 7/2019 | Hickle et al. |
| 10,366,793 B2 | 7/2019 | Apte et al. |
| 10,402,980 B2 | 9/2019 | Mutti et al. |
| 10,413,182 B2 | 9/2019 | Flitsch et al. |
| 10,420,491 B2 | 9/2019 | Rajan et al. |
| 10,423,893 B2 | 9/2019 | Bendfeldt |
| 10,445,846 B2 | 10/2019 | Hwang et al. |
| 10,448,836 B2 | 10/2019 | Darty |
| 10,456,209 B2 | 10/2019 | Peyman |
| 10,467,754 B1 | 11/2019 | Ando et al. |
| 10,468,131 B2 | 11/2019 | Macoviak et al. |
| 10,468,135 B2 | 11/2019 | Lynn et al. |
| 10,478,131 B2 | 11/2019 | Jain et al. |
| 10,523,852 B2 | 12/2019 | Tzvieli et al. |
| 10,524,664 B2 | 1/2020 | Liu et al. |
| 10,524,667 B2 | 1/2020 | Tzvieli et al. |
| 10,537,270 B2 | 1/2020 | Sarussi et al. |
| 10,553,316 B1 | 2/2020 | Neumann |
| 10,553,319 B1 | 2/2020 | Neumann |
| 10,559,386 B1 | 2/2020 | Neumann |
| 10,560,643 B2 | 2/2020 | Barnes et al. |
| 10,568,570 B1 | 2/2020 | Sherpa |
| 10,580,129 B2 | 3/2020 | Lin et al. |
| 10,580,130 B2 | 3/2020 | Frangioni |
| 10,593,431 B1 | 3/2020 | Neumann |
| 10,596,387 B2 | 3/2020 | Walder et al. |
| 10,610,111 B1 | 4/2020 | Tran |
| 10,638,938 B1 | 5/2020 | Tzvieli et al. |
| 10,638,960 B2 | 5/2020 | Hatch |
| 10,656,015 B2 | 5/2020 | McQuilkin et al. |
| 10,660,531 B1 | 5/2020 | Libove et al. |
| 10,660,557 B2 | 5/2020 | Lim et al. |
| 10,666,928 B2 | 5/2020 | Liu |
| 10,667,749 B2 | 6/2020 | Myslinski |
| 10,677,688 B2 | 6/2020 | Rivas et al. |
| 10,682,517 B2 | 6/2020 | Hoffman et al. |
| 10,716,469 B2 | 7/2020 | Krueger |
| 10,719,992 B2 | 7/2020 | Samec et al. |
| 10,722,562 B2 | 7/2020 | Pedersen et al. |
| 2002/0052551 A1 | 5/2002 | Sinclair et al. |
| 2002/0082485 A1 | 6/2002 | Faithfull et al. |
| 2002/0099295 A1 | 7/2002 | Gil et al. |
| 2002/0165439 A1 | 11/2002 | Schmitt |
| 2003/0063300 A1 | 4/2003 | Rubinstenn |
| 2003/0064356 A1 | 4/2003 | Rubinstenn et al. |
| 2003/0065256 A1 | 4/2003 | Rubinstenn |
| 2003/0065552 A1 | 4/2003 | Rubinstenn et al. |
| 2003/0114371 A1 | 6/2003 | Feder et al. |
| 2003/0204070 A1 | 10/2003 | Chen et al. |
| 2003/0224386 A1 | 12/2003 | Guild et al. |
| 2004/0029114 A1 | 2/2004 | Mack et al. |
| 2004/0122702 A1 | 6/2004 | Sabol et al. |
| 2004/0122703 A1 | 6/2004 | Walker et al. |
| 2004/0122704 A1 | 6/2004 | Sabol et al. |
| 2004/0122705 A1 | 6/2004 | Sabol et al. |
| 2004/0122706 A1 | 6/2004 | Walker et al. |
| 2004/0122707 A1 | 6/2004 | Sabol et al. |
| 2004/0122708 A1 | 6/2004 | Avinash et al. |
| 2004/0122709 A1 | 6/2004 | Avinash et al. |
| 2004/0122719 A1 | 6/2004 | Sabol et al. |
| 2004/0122787 A1 | 6/2004 | Avinash et al. |
| 2005/0003487 A1 | 1/2005 | Eaton et al. |
| 2005/0009771 A1 | 1/2005 | Levanon et al. |
| 2005/0014226 A1 | 1/2005 | Ashkenazi et al. |
| 2005/0048620 A1 | 3/2005 | Wu et al. |
| 2005/0124010 A1 | 6/2005 | Short et al. |
| 2005/0130321 A1 | 6/2005 | Nicholson et al. |
| 2005/0152908 A1 | 7/2005 | Liew et al. |
| 2006/0088473 A1 | 4/2006 | Dowding et al. |
| 2006/0257941 A1 | 11/2006 | McDevitt et al. |
| 2007/0014719 A1 | 1/2007 | Reading et al. |
| 2007/0118399 A1 | 5/2007 | Avinash et al. |
| 2007/0123801 A1 | 5/2007 | Goldberger et al. |
| 2007/0135335 A1 | 6/2007 | Collier et al. |
| 2007/0258083 A1 | 11/2007 | Heppell et al. |
| 2008/0072663 A1 | 3/2008 | Keenan et al. |
| 2008/0113358 A1 | 5/2008 | Kapur et al. |
| 2008/0161723 A1 | 7/2008 | Keenan et al. |
| 2008/0200838 A1 | 8/2008 | Goldberger et al. |
| 2008/0241839 A1 | 10/2008 | Potkin et al. |
| 2009/0010908 A1 | 1/2009 | Gow et al. |
| 2009/0032111 A1 | 2/2009 | Tong et al. |
| 2009/0041825 A1 | 2/2009 | Kotov et al. |
| 2009/0070145 A1 | 3/2009 | Haider |
| 2009/0104602 A1 | 4/2009 | Fernandez-Reyes et al. |
| 2009/0156911 A1 | 6/2009 | Rule et al. |
| 2009/0157430 A1 | 6/2009 | Rule et al. |
| 2009/0160656 A1 | 6/2009 | Seetharaman et al. |
| 2009/0270694 A1 | 10/2009 | Hyde et al. |
| 2009/0270700 A1 | 10/2009 | Van Herpen et al. |
| 2009/0271122 A1 | 10/2009 | Hyde et al. |
| 2009/0271347 A1 | 10/2009 | Hyde et al. |
| 2009/0281412 A1 | 11/2009 | Boyden et al. |
| 2009/0287076 A1 | 11/2009 | Boyden et al. |
| 2009/0287094 A1 | 11/2009 | Ferren et al. |
| 2009/0287109 A1 | 11/2009 | Ferren et al. |
| 2009/0287110 A1 | 11/2009 | Ferren et al. |
| 2009/0292212 A1 | 11/2009 | Ferren et al. |
| 2009/0292213 A1 | 11/2009 | Ferren et al. |
| 2009/0292214 A1 | 11/2009 | Ferren et al. |
| 2009/0292222 A1 | 11/2009 | Ferren et al. |
| 2009/0312595 A1 | 12/2009 | Leuthardt et al. |
| 2009/0312668 A1 | 12/2009 | Leuthardt et al. |
| 2009/0318773 A1 | 12/2009 | Jung et al. |
| 2010/0004762 A1 | 1/2010 | Leuthardt et al. |
| 2010/0015583 A1 | 1/2010 | Leuthardt et al. |
| 2010/0017001 A1 | 1/2010 | Leuthardt et al. |
| 2010/0022820 A1 | 1/2010 | Leuthardt et al. |
| 2010/0030089 A1 | 2/2010 | Hyde et al. |
| 2010/0041958 A1 | 2/2010 | Leuthardt et al. |
| 2010/0041964 A1 | 2/2010 | Hyde et al. |
| 2010/0042578 A1 | 2/2010 | Leuthardt et al. |
| 2010/0063368 A1 | 3/2010 | Leuthardt et al. |
| 2010/0069724 A1 | 3/2010 | Leuthardt et al. |
| 2010/0076249 A1 | 3/2010 | Leuthardt et al. |
| 2010/0076691 A1 | 3/2010 | Palucka et al. |
| 2010/0081190 A1 | 4/2010 | Hyde et al. |
| 2010/0081860 A1 | 4/2010 | Leuthardt et al. |
| 2010/0081861 A1 | 4/2010 | Leuthardt et al. |
| 2010/0081915 A1 | 4/2010 | Hyde et al. |
| 2010/0081916 A1 | 4/2010 | Hyde et al. |
| 2010/0081919 A1 | 4/2010 | Hyde et al. |
| 2010/0081923 A1 | 4/2010 | Hyde et al. |
| 2010/0081924 A1 | 4/2010 | Hyde et al. |
| 2010/0081925 A1 | 4/2010 | Hyde et al. |
| 2010/0081926 A1 | 4/2010 | Hyde et al. |
| 2010/0081927 A1 | 4/2010 | Hyde et al. |
| 2010/0081928 A1 | 4/2010 | Hyde et al. |
| 2010/0086481 A1 | 4/2010 | Baird et al. |
| 2010/0100036 A1 | 4/2010 | Leuthardt et al. |
| 2010/0120665 A1 | 5/2010 | Kaleko et al. |
| 2010/0125561 A1 | 5/2010 | Leuthardt et al. |
| 2010/0130811 A1 | 5/2010 | Leuthardt et al. |
| 2010/0145175 A1 | 6/2010 | Soldo et al. |
| 2010/0145412 A1 | 6/2010 | Boyden et al. |
| 2010/0163027 A1 | 7/2010 | Hyde et al. |
| 2010/0168525 A1 | 7/2010 | Hyde et al. |
| 2010/0168529 A1 | 7/2010 | Hyde et al. |
| 2010/0168602 A1 | 7/2010 | Hyde et al. |
| 2010/0185064 A1 | 7/2010 | Bandic et al. |

(56) References Cited

U.S. PATENT DOCUMENTS

| | | |
|---|---|---|
| 2010/0209914 A1 | 8/2010 | Bigwood et al. |
| 2010/0241449 A1 | 9/2010 | Firminger et al. |
| 2010/0268057 A1 | 10/2010 | Firminger et al. |
| 2010/0274577 A1 | 10/2010 | Firminger et al. |
| 2010/0280332 A1 | 11/2010 | Hyde et al. |
| 2010/0305962 A1 | 12/2010 | Firminger et al. |
| 2010/0312579 A1 | 12/2010 | Firminger et al. |
| 2011/0035231 A1 | 2/2011 | Firminger et al. |
| 2011/0097330 A1 | 4/2011 | Horner et al. |
| 2011/0111973 A1 | 5/2011 | Mecklenburg et al. |
| 2011/0160681 A1 | 6/2011 | Dacey, Jr. et al. |
| 2011/0163163 A1 | 7/2011 | Rowe |
| 2011/0189680 A1 | 8/2011 | Keown et al. |
| 2011/0190613 A1 | 8/2011 | Zhang et al. |
| 2011/0236903 A1 | 8/2011 | McClelland et al. |
| 2011/0251099 A1 | 10/2011 | Visvanathan et al. |
| 2011/0257892 A1 | 10/2011 | Selifonov et al. |
| 2011/0306518 A1 | 12/2011 | Wohlgemuth et al. |
| 2012/0030776 A1 | 2/2012 | Combs et al. |
| 2012/0034157 A1 | 2/2012 | Hyde et al. |
| 2012/0059778 A1 | 3/2012 | Soykan et al. |
| 2012/0072124 A1 | 3/2012 | Radich et al. |
| 2012/0115248 A1 | 5/2012 | Ansyln et al. |
| 2012/0119089 A1* | 5/2012 | Sanchez del Rio Saez ............... A61B 5/1172 250/341.8 |
| 2012/0130196 A1 | 5/2012 | Jain et al. |
| 2012/0130201 A1 | 5/2012 | Jain |
| 2012/0130202 A1 | 5/2012 | Jain |
| 2012/0150003 A1 | 6/2012 | Zhang |
| 2012/0178100 A1 | 7/2012 | Wagner et al. |
| 2012/0190947 A1 | 7/2012 | Chon et al. |
| 2012/0190964 A1 | 7/2012 | Hyde et al. |
| 2012/0197621 A1 | 8/2012 | Jain |
| 2012/0197622 A1 | 8/2012 | Jain |
| 2012/0264686 A9 | 10/2012 | Guyon et al. |
| 2012/0265546 A1 | 10/2012 | Hwang et al. |
| 2012/0265547 A1 | 10/2012 | Hwang et al. |
| 2012/0265548 A1 | 10/2012 | Hwang et al. |
| 2012/0265591 A1 | 10/2012 | Hwang et al. |
| 2012/0272341 A1 | 10/2012 | Combs et al. |
| 2012/0277999 A1 | 11/2012 | Somogyi et al. |
| 2012/0282353 A1 | 11/2012 | Roth et al. |
| 2012/0321759 A1 | 12/2012 | Marinkovich et al. |
| 2012/0323127 A1 | 12/2012 | Boyden et al. |
| 2013/0035569 A1 | 2/2013 | Heanue et al. |
| 2013/0071837 A1 | 3/2013 | Winters-Hilt et al. |
| 2013/0123592 A1 | 5/2013 | Rule |
| 2013/0160150 A1 | 6/2013 | Leibel et al. |
| 2014/0011879 A1 | 1/2014 | Baribaud et al. |
| 2014/0016116 A1 | 1/2014 | Maier et al. |
| 2014/0107080 A1 | 4/2014 | Koga et al. |
| 2014/0163409 A1 | 6/2014 | Arndt |
| 2014/0199273 A1 | 7/2014 | Cesano et al. |
| 2014/0200511 A1 | 7/2014 | Boyden et al. |
| 2014/0247155 A1 | 9/2014 | Proud |
| 2014/0276090 A1 | 9/2014 | Breed |
| 2014/0296693 A1 | 10/2014 | Binder et al. |
| 2014/0308930 A1 | 10/2014 | Tran |
| 2014/0378795 A1 | 12/2014 | McKenna |
| 2015/0068069 A1 | 3/2015 | Tran et al. |
| 2015/0118689 A1 | 4/2015 | Egan et al. |
| 2015/0150460 A1 | 6/2015 | Krishnaswamy et al. |
| 2015/0205992 A1 | 7/2015 | Rowe |
| 2015/0269825 A1 | 9/2015 | Tran |
| 2015/0287191 A1 | 10/2015 | Koruga et al. |
| 2015/0313532 A1 | 11/2015 | Marinkovich et al. |
| 2015/0327799 A1 | 11/2015 | Vosch et al. |
| 2015/0351655 A1 | 12/2015 | Coleman |
| 2015/0359467 A1 | 12/2015 | Tran |
| 2016/0103123 A1 | 4/2016 | Holmes et al. |
| 2016/0157725 A1 | 6/2016 | Munoz |
| 2016/0175408 A1 | 6/2016 | Chang et al. |
| 2016/0194718 A1 | 7/2016 | Lane et al. |
| 2016/0228008 A1 | 8/2016 | Lee |
| 2016/0269411 A1 | 9/2016 | Malachi |
| 2016/0317744 A1 | 11/2016 | Rule |
| 2016/0360980 A1* | 12/2016 | Sinha .................. A61B 5/7264 |
| 2016/0371451 A1 | 12/2016 | Rule et al. |
| 2017/0020391 A1 | 1/2017 | Flitsch et al. |
| 2017/0020431 A1 | 1/2017 | Flitsch et al. |
| 2017/0020440 A1 | 1/2017 | Flitsch et al. |
| 2017/0020441 A1 | 1/2017 | Flitsch et al. |
| 2017/0020442 A1 | 1/2017 | Flitsch et al. |
| 2017/0024530 A1 | 1/2017 | Flitsch et al. |
| 2017/0024555 A1 | 1/2017 | Flitsch et al. |
| 2017/0024771 A1 | 1/2017 | Flitsch et al. |
| 2017/0026790 A1 | 1/2017 | Flitsch et al. |
| 2017/0035348 A1 | 2/2017 | Bandic et al. |
| 2017/0049377 A1 | 2/2017 | Littell |
| 2017/0071516 A1* | 3/2017 | Bhagat .............. A61B 5/14551 |
| 2017/0086672 A1 | 3/2017 | Tran |
| 2017/0105681 A1 | 4/2017 | Singh et al. |
| 2017/0119235 A1 | 5/2017 | Hyde et al. |
| 2017/0119236 A1 | 5/2017 | Hyde et al. |
| 2017/0119278 A1 | 5/2017 | Hyde et al. |
| 2017/0127959 A1 | 5/2017 | Paulussen et al. |
| 2017/0150903 A1 | 6/2017 | Barnes et al. |
| 2017/0173262 A1 | 6/2017 | Veltz |
| 2017/0177812 A1 | 6/2017 | Sjölund |
| 2017/0188943 A1 | 7/2017 | Braig et al. |
| 2017/0189629 A1 | 7/2017 | Newberry |
| 2017/0209049 A1 | 7/2017 | Wang et al. |
| 2017/0216518 A1 | 8/2017 | Davis et al. |
| 2017/0231560 A1 | 8/2017 | Hyde et al. |
| 2017/0246473 A1 | 8/2017 | Marinkovich et al. |
| 2017/0262614 A1 | 9/2017 | Vishnubhatla et al. |
| 2017/0308813 A1 | 10/2017 | Boyden et al. |
| 2017/0333454 A1 | 11/2017 | Simard |
| 2017/0343634 A1 | 11/2017 | Lencz et al. |
| 2017/0349894 A1 | 12/2017 | Dahlman et al. |
| 2017/0349948 A1 | 12/2017 | Lo et al. |
| 2017/0357760 A1 | 12/2017 | Han et al. |
| 2017/0363633 A1 | 12/2017 | Cesano et al. |
| 2018/0045654 A1 | 2/2018 | Park et al. |
| 2018/0110462 A1 | 4/2018 | Asvadi et al. |
| 2018/0125430 A1 | 5/2018 | Al-Ali et al. |
| 2018/0161658 A1 | 6/2018 | Felker |
| 2018/0168459 A1 | 6/2018 | Tran |
| 2018/0168488 A1 | 6/2018 | Jones et al. |
| 2018/0182475 A1 | 6/2018 | Cossler et al. |
| 2018/0184972 A1 | 7/2018 | Carmi et al. |
| 2018/0197636 A1 | 7/2018 | Firminger et al. |
| 2018/0207198 A1 | 7/2018 | Salome et al. |
| 2018/0214088 A1 | 8/2018 | Newberry |
| 2018/0242844 A1 | 8/2018 | Liu et al. |
| 2018/0253840 A1 | 9/2018 | Tran |
| 2018/0259420 A1 | 9/2018 | Rule et al. |
| 2018/0263555 A1 | 9/2018 | Rule et al. |
| 2018/0310828 A1 | 11/2018 | DiMaio et al. |
| 2018/0310862 A1 | 11/2018 | Khoja et al. |
| 2018/0311510 A1 | 11/2018 | Sjolund et al. |
| 2018/0318529 A1 | 11/2018 | Davidson et al. |
| 2018/0344228 A1 | 12/2018 | Yelin |
| 2018/0344231 A1 | 12/2018 | Butler et al. |
| 2018/0360320 A1 | 12/2018 | Werahera et al. |
| 2018/0372715 A1 | 12/2018 | Kluckner et al. |
| 2019/0000349 A1 | 1/2019 | Narayan et al. |
| 2019/0022152 A1 | 1/2019 | Elinav et al. |
| 2019/0062813 A1 | 2/2019 | Amin |
| 2019/0065961 A1 | 2/2019 | Szu |
| 2019/0081497 A1 | 3/2019 | Pugh et al. |
| 2019/0082990 A1 | 3/2019 | Poltorak |
| 2019/0083805 A1 | 3/2019 | Etkin |
| 2019/0085324 A1 | 3/2019 | Regev et al. |
| 2019/0114469 A1 | 4/2019 | Sartor et al. |
| 2019/0117146 A1 | 4/2019 | Barbour et al. |
| 2019/0125272 A1 | 5/2019 | Szu |
| 2019/0125361 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |

(56) References Cited

U.S. PATENT DOCUMENTS

| | | |
|---|---|---|
| 2019/0125459 A1 | 5/2019 | Shelton, IV et al. |
| 2019/0138907 A1 | 5/2019 | Szu |
| 2019/0148013 A1 | 5/2019 | Pulitzer et al. |
| 2019/0159735 A1 | 5/2019 | Rundo et al. |
| 2019/0192855 A1 | 6/2019 | Bharmi et al. |
| 2019/0200977 A1 | 7/2019 | Shelton, IV et al. |
| 2019/0201124 A1 | 7/2019 | Shelton, IV et al. |
| 2019/0201136 A1 | 7/2019 | Shelton, IV et al. |
| 2019/0201848 A1 | 7/2019 | Rao |
| 2019/0206562 A1 | 7/2019 | Shelton, IV et al. |
| 2019/0206563 A1 | 7/2019 | Shelton, IV et al. |
| 2019/0206565 A1 | 7/2019 | Shelton, IV |
| 2019/0206576 A1 | 7/2019 | Shelton, IV et al. |
| 2019/0212345 A1 | 7/2019 | Lam et al. |
| 2019/0214147 A1 | 7/2019 | Ariely |
| 2019/0216326 A1 | 7/2019 | Cross et al. |
| 2019/0223791 A1 | 7/2019 | Sayani et al. |
| 2019/0224441 A1 | 7/2019 | Poltorak |
| 2019/0231249 A1 | 8/2019 | Dascalu |
| 2019/0231903 A1 | 8/2019 | Bradbury et al. |
| 2019/0237186 A1 | 8/2019 | El-Baz et al. |
| 2019/0247650 A1 | 8/2019 | Tran |
| 2019/0247662 A1 | 8/2019 | Poltroak |
| 2019/0256924 A1 | 8/2019 | Vogelstein et al. |
| 2019/0277870 A1 | 9/2019 | Kluckner et al. |
| 2019/0282141 A1 | 9/2019 | Causey, III et al. |
| 2019/0290172 A1 | 9/2019 | Hadad et al. |
| 2019/0311191 A1 | 10/2019 | Aarabi et al. |
| 2019/0313966 A1 | 10/2019 | Lanzkowsky |
| 2019/0321394 A1 | 10/2019 | Wager et al. |
| 2019/0321583 A1 | 10/2019 | Poltorak |
| 2019/0325991 A1 | 10/2019 | Ishii |
| 2019/0330350 A1 | 10/2019 | Freeman et al. |
| 2019/0332757 A1 | 10/2019 | Chen et al. |
| 2019/0336678 A1 | 11/2019 | Rule |
| 2019/0351031 A1 | 11/2019 | Wang et al. |
| 2019/0392931 A1 | 12/2019 | Abousy et al. |
| 2020/0004336 A1 | 1/2020 | Newberry |
| 2020/0020247 A1 | 1/2020 | Simpson et al. |
| 2020/0022560 A1 | 1/2020 | Oosake |
| 2020/0033258 A1 | 1/2020 | Benni |
| 2020/0057661 A1 | 2/2020 | Bendfeldt |
| 2020/0066405 A1 | 2/2020 | Peyman |
| 2020/0077892 A1 | 3/2020 | Tran |
| 2020/0082925 A1 | 3/2020 | Iwata |
| 2020/0085312 A1 | 3/2020 | Tzvieli et al. |
| 2020/0086078 A1 | 3/2020 | Poltorak |
| 2020/0093387 A1 | 3/2020 | Gutierrez et al. |
| 2020/0093427 A1 | 3/2020 | Akhbardeh et al. |
| 2020/0097814 A1 | 3/2020 | Devesa |
| 2020/0098461 A1 | 3/2020 | Macoviak et al. |
| 2020/0114164 A1 | 4/2020 | Bourke, Jr. et al. |
| 2020/0118458 A1 | 4/2020 | Shriberg et al. |
| 2020/0121262 A1* | 4/2020 | De Haan .............. A61B 5/7246 |
| 2020/0126226 A1 | 4/2020 | Adiri et al. |
| 2020/0126227 A1 | 4/2020 | Adiri et al. |
| 2020/0126664 A1 | 4/2020 | Sato |
| 2020/0134672 A1 | 4/2020 | el Kaliouby et al. |
| 2020/0135042 A1 | 4/2020 | An et al. |
| 2020/0138360 A1 | 5/2020 | Fan et al. |
| 2020/0151878 A1 | 5/2020 | Kluckner et al. |
| 2020/0155001 A1 | 5/2020 | Perez et al. |
| 2020/0158745 A1 | 5/2020 | Tian et al. |
| 2020/0160998 A1 | 5/2020 | Ward et al. |
| 2020/0163602 A1 | 5/2020 | Pareddy et al. |
| 2020/0164132 A1 | 5/2020 | Loderer et al. |
| 2020/0164209 A1 | 5/2020 | Hogg et al. |
| 2020/0166760 A1 | 5/2020 | Samec et al. |
| 2020/0176099 A1 | 6/2020 | Welss et al. |
| 2020/0179717 A1 | 6/2020 | Lee et al. |
| 2020/0182778 A1 | 6/2020 | Srivastava |
| 2020/0185100 A1 | 6/2020 | Francois |
| 2020/0187860 A1 | 6/2020 | Myslinski |
| 2020/0188164 A1 | 6/2020 | Myslinski |
| 2020/0188708 A1 | 6/2020 | Myslinski |
| 2020/0193587 A1 | 6/2020 | Mairhofer |
| 2020/0193597 A1 | 6/2020 | Fan et al. |
| 2020/0196968 A1 | 6/2020 | Toyoda et al. |
| 2020/0209214 A1 | 7/2020 | Zohar et al. |
| 2020/0211692 A1 | 7/2020 | Kalafut et al. |
| 2020/0211709 A1 | 7/2020 | Devesa |
| 2020/0211713 A1 | 7/2020 | Shadforth et al. |
| 2020/0211716 A1 | 7/2020 | Lefkofsky et al. |
| 2020/0214571 A1 | 7/2020 | Bradbury et al. |
| 2020/0222711 A1 | 7/2020 | Walder et al. |
| 2020/0227144 A1 | 7/2020 | Callicoat et al. |
| 2020/0237274 A1 | 7/2020 | Hatch |

FOREIGN PATENT DOCUMENTS

| | | |
|---|---|---|
| AU | 2018201076 A1 | 3/2018 |
| CA | 2311487 A1 | 11/1999 |
| EP | 1712226 A2 | 10/2006 |
| EP | 2416270 A2 | 2/2012 |
| EP | 2397969 B1 | 4/2013 |
| EP | 2389573 B1 | 1/2016 |
| EP | 1773943 B1 | 3/2016 |
| EP | 2355690 B1 | 1/2018 |
| EP | 3150239 B1 | 1/2019 |
| EP | 3663785 A1 | 6/2020 |
| EP | 3419519 B1 | 7/2020 |
| EP | 3160554 B1 | 10/2021 |
| EP | 3419502 B1 | 5/2022 |
| EP | 2678070 B1 | 10/2022 |
| EP | 3426131 B1 | 11/2022 |
| IN | 276599 B | 10/2016 |
| IN | 292623 B | 9/2018 |
| IN | 432622 B | 5/2023 |
| IN | 488928 B | 12/2023 |
| WO | 9639928 A1 | 12/1996 |
| WO | 9939633 A1 | 8/1999 |
| WO | 0042560 A2 | 7/2000 |
| WO | 0067635 A1 | 11/2000 |
| WO | 0130231 A2 | 5/2001 |
| WO | 0215818 A2 | 2/2002 |
| WO | 02032406 A3 | 4/2002 |
| WO | 0239873 A2 | 5/2002 |
| WO | 02085195 A2 | 10/2002 |
| WO | 02086478 A3 | 10/2002 |
| WO | 02086500 A3 | 10/2002 |
| WO | 2006110172 A2 | 10/2006 |
| WO | 2007030124 A2 | 3/2007 |
| WO | 2007050902 A1 | 5/2007 |
| WO | 2007138598 A2 | 12/2007 |
| WO | 2007144148 A1 | 12/2007 |
| WO | 2008086311 A2 | 7/2008 |
| WO | 2008106644 A2 | 9/2008 |
| WO | 2008111994 A1 | 9/2008 |
| WO | 2008144613 A1 | 11/2008 |
| WO | 2009089292 A1 | 7/2009 |
| WO | 2010002278 A1 | 1/2010 |
| WO | 2011031351 A1 | 3/2011 |
| WO | 2011127467 A1 | 10/2011 |
| WO | 2012159012 A1 | 11/2012 |
| WO | 2013052318 A1 | 4/2013 |
| WO | 2014137913 A1 | 9/2014 |
| WO | 2014164717 A1 | 10/2014 |
| WO | 2014165607 A2 | 10/2014 |
| WO | 2015119520 A1 | 8/2015 |
| WO | 2015130333 A1 | 9/2015 |
| WO | 2015176043 A1 | 11/2015 |
| WO | 2015197385 A1 | 12/2015 |
| WO | 2016001922 A1 | 1/2016 |
| WO | 2017075009 A1 | 5/2017 |
| WO | 2017205047 A2 | 11/2017 |
| WO | 2017206888 A1 | 12/2017 |
| WO | 2017216724 A1 | 12/2017 |
| WO | 2017217597 A1 | 12/2017 |
| WO | 2018035387 A1 | 2/2018 |
| WO | 2018057058 A1 | 3/2018 |
| WO | 2018060996 A1 | 4/2018 |
| WO | 2018064569 A1 | 4/2018 |
| WO | 2018069789 A1 | 4/2018 |
| WO | 2018081423 A1 | 5/2018 |

(56) References Cited

FOREIGN PATENT DOCUMENTS

| WO | 2018102740 A1 | 6/2018 |
| --- | --- | --- |
| WO | 2018112459 A1 | 6/2018 |
| WO | 2019043446 A1 | 3/2019 |
| WO | 2019060298 A1 | 3/2019 |
| WO | 2019084517 A1 | 5/2019 |
| WO | 2019086955 A2 | 5/2019 |
| WO | 2019102277 A1 | 5/2019 |
| WO | 2019113512 A1 | 6/2019 |
| WO | 2019118941 A2 | 6/2019 |
| WO | 2019126774 A1 | 6/2019 |
| WO | 2019130313 A1 | 7/2019 |
| WO | 2019132915 A1 | 7/2019 |
| WO | 2019136513 A1 | 7/2019 |
| WO | 2019141869 A1 | 7/2019 |
| WO | 2019157277 A1 | 8/2019 |
| WO | 2019161411 A1 | 8/2019 |
| WO | 2019173237 A1 | 9/2019 |
| WO | 2019173283 A1 | 9/2019 |
| WO | 2019183399 A1 | 9/2019 |
| WO | 2019210272 A1 | 10/2019 |
| WO | 2019212833 A1 | 11/2019 |
| WO | 2019213133 A1 | 11/2019 |
| WO | 2019213783 A1 | 11/2019 |
| WO | 2019237191 A1 | 12/2019 |
| WO | 2019246239 A1 | 12/2019 |
| WO | 2020006145 A1 | 1/2020 |
| WO | 2020025684 A1 | 2/2020 |
| WO | 2020025696 A1 | 2/2020 |
| WO | 2020035852 A2 | 2/2020 |
| WO | 2020036620 A1 | 2/2020 |
| WO | 2020041204 A1 | 2/2020 |

OTHER PUBLICATIONS

Rice et al., Noninvasive hemoglobin monitoring: how accurate is enough?, Anesthesia & Analgesia, 2013, 117(4):902-907.

Scully et al., Physiological parameter monitoring from optical recordings with a mobile phone, IEEE Transactions on Biomedical Engineering, 2011, 59(2):303-306.

Siddiqui et al., A pulse rate estimation algorithm using PPG and smartphone camera, Journal of Medical Systems, 2016, 40(126):1-6.

Smith et al., Second window for in vivo imaging, Nature Nanotechnology, 2009, 4(11):710-711.

STAT Innovations, Making Screening for Anaemia as Simple as Taking a Selfie, Retrieved from https://web.archive.org/web/20221004232209/https://www.statinnovations.com/eyenaemia, Copyright 2018 STAT Innovations Pty. Ltd., 4 pages.

Suner et al., Non-invasive determination of hemoglobin by digital photography of palpebral conjunctiva, The Journal of Emergency Medicine, 2007, 33(2):105-111.

Tamura et al., Wearable photoplethysmographic sensors—past and present, Electronics, 2014, 3(2):282-302.

Uguz et al., Multifunctional photoplethysmography sensor design for respiratory and cardiovascular diagnosis, in "World Congress on Medical Physics and Biomedical Engineering 2018: Jun. 3-8, 2018, Prague, Czech Republic," Springer, vol. 2, 2019, pp. 905-909.

Wang et al., HemaApp: noninvasive blood screening of hemoglobin using smartphone cameras, Proceeding of the 2016 ACM International Joint Conference on Pervasive and Ubiquitous Computing, 2016, 12 pages.

Wang et al., HemaApp IR: noninvasive hemoglobin measurement using unmodified smartphone cameras and built-in LEDs, Proceedings of the 2017 ACM International Joint Conference on Pervasive and Ubiquitous Computing and Proceedings of the 2017 ACM International Symposium on Wearable Computers, 2017, pp. 305-308.

Wu et al., Screening for iron deficiency, Pediatrics in Review, 2002, 23(5):171-178.

Yamakoshi et al., Pulse glucometry: a new approach for noninvasive blood glucose measurement using instantaneous differential near-infrared spectrophotometry, Journal of Biomedical Optics, 2006, 11(5):054028, pp. 1-9.

Zhang, Photoplethysmography-based heart rate monitoring in physical activities via joint sparse spectrum reconstruction, IEEE Transactions on Biomedical Engineering, arXiv preprint, arXiv:1503.00688, 2015, 9 pages.

Zhang et al., Evaluating photoplethysmogram as a real-time cognitive load assessment during game playing, International Journal of Human-Computer Interaction, 2018, 34(8):695-706.

Zheng et al., The preliminary investigation of imaging photoplethysmographic system, Journal of Physics: Conference Series, IoP Publishing, 2007, 85(012031):1-5.

PCT International Search Report and Written Opinion, PCT/US2019/020675, May 23, 2019, 28 pages.

Ahsan et al., A novel real-time non-invasive hemoglobin level detection using video images from smartphone camera, 2017 IEEE 41st Annual Computer Software and Applications Conference (COMPSAC), IEEE, 2017, vol. 1, 15 pages.

Allen, Photoplethysmography and its application in clinical physiological measurement, Physiological Measurement, 2007, 28(3):R1-R39.

Anderson, The accuracy of pulse oximetry in neonates: effects of fetal hemoglobin and bilirubin, Journal of Perinatology, 1987, 7(4):323.

Anggraeni et al., Non-invasive self-care anemia detection during pregnancy using a smartphone camera, IOP Conference Series: Materials Science and Engineering, 2017, 172(012030):1-6.

Benenson et al., Sickle cell disease: bone, joint, muscle, and motor complications, Orthopaedic Nursing, 2018, 37(4):221-227.

Bui et al., Pho2: Smartphone based blood oxygen level measurement systems using near-ir and red wave-guided light, Proceedings of the 15th ACM Conference on Embedded Network Sensor Systems, 2017, 14 pages.

Carroll et al., Laser-tissue interactions, Clinics in Dermatology, 2006, 24(1):2-7.

Causey et al., Validation of noninvasive hemoglobin measurements using the Masimo Radical-7 SpHb Station, The American Journal of Surgery, 2011, 201(5):592-598.

Centers for Disease Control and Prevention, Sickle Cell Disease (SCD), Retrieved from https://www.cdc.gov/ncbddd/sicklecell/index.html, Accessed in 2017, 4 pages.

Challoner, Photoelectric plethysmography for estimating cutaneous blood flow, in "Non-Invasive Physiological Measurements," Academic Press, 1979, Chapter 6, pp. 125-151.

Chang et al., Visible light optical spectroscopy is sensitive to neovascularization in the dysplastic cervix, Journal of Biomedical Optics, 2010, 15(5):057006, pp. 1-9.

Chanklan et al., Runoff prediction with a combined artificial neural network and support vector regression, International Journal of Machine Learning and Computing, 2018, 8(1):39-43.

Collings et al., Non-invasive detection of anaemia using digital photographs of the conjunctiva, PloS One, 2016, 11(4):e0153286, pp. 1-10.

Dantu et al., Non-invasive blood glucose monitor based on spectroscopy using a smartphone, 2014 36th Annual International Conference of the IEEE Engineering in Medicine and Biology Society, IEEE, 2014, pp. 3695-3698.

Edwards et al., Smartphone based optical spectrometer for diffusive reflectance spectroscopic measurement of hemoglobin, Scientific Reports, 2017, 7(1):12224, pp. 1-7.

Giavarina, Understanding bland altman analysis, Biochemia Medica, 2015, 25(2):141-151.

Gordy et al., Spectrophotometric studies: XVI. Determination of the oxygen saturation of blood by a simplified technique, applicable to standard equipment, Journal of Biological Chemistry, 1957, 227(1):285-299.

Hadar et al., Precision and accuracy of noninvasive hemoglobin measurements during pregnancy, The Journal of Maternal-Fetal and Neonatal Medicine, 2012, 25(12):2503-2506.

Hasan et al., Road structure analysis using GPS information, 2013 International Conference on Electrical Information and Communication Technology (EICT), IEEE, 2014, 6 pages.

Hasan et al., Pain level detection from facial image captured by smartphone, Journal of Information Processing, 2016, 24(4):598-608.

(56) References Cited

OTHER PUBLICATIONS

Hasan et al., A novel process to extract important information from invisible video captured by smartphone, 2017 IEEE Great Lakes Biomedical Conference (GLBC), IEEE, 2017, 2 pages.

Hasan et al., Analyzing the existing noninvasive hemoglobin measurement techniques, 2017 IEEE 8th Annual Ubiquitous Computing, Electronics and Mobile Communication Conference (UEMCON), IEEE, 2017, pp. 442-448.

Hasan et al., Bild (big image in less dimension): A novel technique for image feature selection to apply partial least square algorithm, 2017 IEEE Great Lakes Biomedical Conference (GLBC), IEEE, 2017, 2 pages.

Hasan et al., RGB pixel analysis of fingertip video image captured from sickle cell patient with low and high level of hemoglobin, 2017 IEEE 8th Annual Ubiquitous Computing, Electronics and Mobile Communication Conference (UEMCON), IEEE, 2017, pp. 499-505.

Hasan et al., A novel technique of noninvasive hemoglobin level measurement using hsv value of fingertip image, arXiv preprint, arXiv:1910.02579, 2019, 23 pages.

Hemoglobe, Hemoglobe: See Who is Nearby with Hemoglobe, Retrieved from https://hemoglobe.com/archive/, Accessed on Mar. 1, 2018, 3 pages.

Johnson et al., Smartphone-based light and sound intensity calculation application for accessibility measurement, InRESNA Annual Conference, 2015, 5 pages.

Jonathan et al., Investigating a smartphone imaging unit for photoplethysmography, Physiological Measurement, 2010, 31(11):N79.

Jonathan et al., Cellular phone-based photoplethysmographic imaging, Journal of Biophotonics, 2010, 1-4, 5 pages.

Jones, Medical electro-optics: measurements in the human microcirculation, Physics in Technology, 1987, 18(2):79.

Kalra, Developing FE Human Models from Medical Images, in "Basic Finite Element Method as Applied to Injury Biomechanics," Academic Press, 2018, Chapter 9, pp. 389-415.

Kawsar et al., A novel activity detection system using plantar pressure sensors and smartphone, 2015 IEEE 39th Annual International Computers, Software & Applications Conference, IEEE, 2015, vol. 1., pp. 44-49.

Kawsar et al., Activity detection using time-delay embedding in multi-modal sensor system, Inclusive Smart Cities and Digital Health: 14th International Conference on Smart Homes and Health Telematics, ICOST 2016, Proceedings 14, 2016, pp. 489-499.

Keijzer et al., Light distributions in artery tissue: Monte Carlo simulations for finite-diameter laser beams, Lasers in Surgery and Medicine, 1989, 9(2):148-154.

Le, The prevalence of anemia and moderate-severe anemia in the US population (NHANES 2003-2012), PloS One, 2016, 11(11):e0166635, pp. 1-14.

Li et al., Noninvasive hemoglobin measurement based on optimizing Dynamic Spectrum method, Spectroscopy Letters, 2017, 50(3):164-170.

Loonsk, BioSense—A national initiative for early detection and quantification of public health emergencies, Morbidity and Mortality Weekly Report, 2004, 53, Supplement: Syndromic Surveillance, pp. 53-55.

Lisboa, A review of evidence of health benefit from artificial neural networks in medical intervention, Neural Networks, 2002, 15(1):11-39.

Lisboa et al., The use of artificial neural networks in decision support in cancer: a systematic review, Neural Networks, 2006, 19(4):408-415.

Mahmud et al., Designing Access Control Model and Enforcing Security Policies Using Permis for a Smart Item E-Health Scenario, International Journal of Engineering Science and Technology, 2010, 2(8):3777-3787.

Masimo, Masimo rainbow® Pulse CO-Oximetry, Retrieved from https://professional.masimo.com/technology/co-oximetry/rainbow/, Copyright 2024 Masimo, 5 pages.

McMillan, These Medical Apps Have Doctors and the FDA Worried, Retrieved from https://www.wired.com/2014/07/medical-apps/, Jul. 29, 2014, 14 pages.

Mendelson, Pulse oximetry: theory and applications for noninvasive monitoring, Clinical Chemistry, 1992, 38(9):1601-1607.

Millasseau et al., Contour analysis of the photoplethysmographic pulse measured at the finger, Journal of Hypertension, 2006, 24(8):1449-1456.

Mukaka, Statistics Corner: A guide to appropriate use of Correlation coefficient in medical research, Malawi Medical Journal, 2012, 24(3):69-71.

Nam et al., Photoplethysmography signal analysis for optimal region-of-interest determination in video imaging on a built-in smartphone under different conditions, Sensors, 2017, 17(10):2385, pp. 1-18.

Pelegris et al., A novel method to detect heart beat rate using a mobile phone, 32nd Annual International Conference of the IEEE Engineering in Medicine and Biology, IEEE, 2010, 5 pages.

Punter-Villagrasa et al., An instantaneous low-cost point-of-care anemia detection device, Sensors, 2015, 15(2):4564-4577.

Qui et al., Recent progress in upconversion photodynamic therapy, Nanomaterials, 2018, 8(5):344, pp. 1-18.

* cited by examiner

METHOD AND APPARATUS FOR NON-INVASIVE HEMOGLOBIN LEVEL PREDICTION

CROSS-REFERENCE TO RELATED APPLICATIONS

This application represents the U.S. national stage entry of International Application No. PCT/US2019/020675 filed on Mar. 5, 2019, which claims the benefit of U.S. Provisional patent application Ser. No. 62/638,630, filed on Mar. 5, 2018, which disclosures are incorporated herein by reference in their entirety.

BACKGROUND

Hematologic diseases are a major global public health problem. The principle constituent of blood is hemoglobin in red blood cells. Broadly, hematologic diseases are of two major types: the anemias and hematologic disorders—primarily hemoglobinopathies. Hemoglobin functions to carry oxygen to body tissues, which activity is compromised with disease. Iron-deficiency anemia occurs in 2 billion people worldwide, and during the past decade, the numbers of people affected has increased. The World Health Organization (WHO) has estimated that anemia affects about 25% of the global population, and an average of 5.6% of the US population. Anemia is particularly problematic in children, because it enhances the risk of cognitive development impairment, and in pregnant women, who suffer higher maternal mortality rates. Many of those suffering from anemia are in developing countries where medical resources are limited.

The most common hematological disorder is sickle cell hemoglobinopathy, called sickle cell disease (SCD). SCD patients are anemic and have abnormal, sickle-shaped red blood cells, the percentages of which increase under stress (such as with infections) causing small vessel obstruction. The most common clinical problems with SCD patient are crises with acute and sever musculoskeletal pain. In the United States, according to the Centers for Disease Control and Prevention (CDC), about 100,000 Americans have SCD and the cases numbers are increasing. Approximately one in 365 African Americans and one in 16,300 Hispanic Americans have SCD.

Currently, the most common measure to assess for hematologic disease is a laboratory plasma hemoglobin (Hgb) test, which determines the concentration of hemoglobin in the blood. These laboratory tests are done on venous or capillary blood specimens obtained invasively, most commonly with drawing blood from a vein, which involves insertion of a needle. Patients therefore can feel discomfort, pain, numbness, or a shocking sensation. Itching or burning at the collection site is also common. These procedures can be particularly traumatic for children and mentally disabled persons. Additionally, these tests require travel to a medical facility, and can be expensive. While there are some point-of-care systems for hemoglobin assess, these are also expensive. In sum, the current technology is inconvenient, costly, slow, uncomfortable and for many not readily accessible.

Some non-invasive point-of-care tools for assessment of hemoglobin levels are available. However, these tools are expensive, have poor performance measures, and require specific training for proper operation and appropriate use. As a result, only large research centers and hospitals can purchase, operate, and maintain these systems.

Recently, smartphone-based hemoglobin measurement technologies have been developed for hemoglobin level assessment. Some of these technologies rely on analysis of the lower eyelid conjunctiva, which has been shown to be useful because the conjunctival mucosa is thin and the underlying micro-vessels are easily seen. One such smartphone-based system compares conjunctival pallor with an eye color chart. Estimation of precise hemoglobin levels with these systems is presently poor.

In these circumstances, a non-invasive, easy-to-use, inexpensive measure of hemoglobin levels is desirable to improve access to diagnostics and to provide safe management of patients with hematologic disease.

SUMMARY

In one aspect, the present disclosure provides a method for non-invasively blood hemoglobin levels. The method comprises acquiring a time-based series of images of the finger ventral pad-tip illuminated from the dorsal side of the finger with a near infrared light responsive to blood hemoglobin, and white light, and acquiring a second time-based series of images of the finger ventral pad-tip illuminated from the dorsal side of the finger with a near infrared light responsive to blood plasma, and white light. Each image in each of the first and second time-based series is divided into groups of blocks. A time series signal is generated from each block, and at least one Photoplethysmography (PPG) cycle is identified from each of the time series signals, including a systolic peak and a diastolic peak. The PPG cycles are processed to determine blood hemoglobin levels.

The step of acquiring a time-based series of images can include acquiring a first and a second video. The video can be separated into frames, each frame comprising an image.

The near infrared light responsive to blood hemoglobin can have a wavelength of between 800 and 950 nm, and the near infrared light responsive to plasma can have a wavelength of 1070 nm. The near infrared light responsive to blood hemoglobin can have a wavelength of 850 nm.

The method can include calculating a ratio of the PPG signal of the first time-based series of images of a blood flow illuminated with a near infrared light responsive to blood hemoglobin, to the second time-based series of the images of a blood flow illuminated with a near infrared light responsive to blood plasma.

The method can also comprise identifying at least one feature in each of the PPG cycles, and the feature can be used to determine the hemoglobin level. The feature can comprise at least one of a relative augmentation of a PPG, an area under the systolic peak; an area under a diastolic peak, a slope of the systolic peak, a slope of the diastolic peak, a relative timestamp value of the peak, a normalized PPG rise time, a pulse transit time (PTT), a pulse shape, or an amplitude.

The step of processing the PPG can comprise analyzing the PPG signals using a prediction model constructed using a support vector machine regression.

The step of generating a time series signal for each of the first and second time-based series of images comprises acquiring red green blue (RGB) digital images of a blood flow. Here, the step of subdividing each image into a plurality of blocks further comprises subdividing each image into a plurality of blocks further comprising a defined number of pixels, calculating a mean intensity value for the red pixels in each block, generating the time series signal identifying each image in the series versus an average value of a block, and subsequently identifying at least one PPG signal in each time series.

In another aspect, a system for non-invasive analysis of a hemoglobin level is disclosed. The system comprises a camera, a first lighting device comprising a near infrared light of a wavelength responsive to blood hemoglobin and adapted to provide images of a finger of a subject, and a second lighting device comprising a near infrared light of wavelength responsive to blood plasma and adapted to provide images of a finger of a subject, and at least one processor. The processor is programmed to receive a first time series of images of a finger of a subject while illuminated by the first lighting device, the first time series of images acquired under conditions selected to capture at least one complete detailed Photoplethysmography (PPG) cycle representative of blood hemoglobin and to receive a second time series of images of the finger while illuminated by the second lighting device, the second time series of images acquired under conditions to capture at least one complete detailed PPG cycle representative of plasma. The processor is further programmed to identify at least one feature in the PPG cycle representative of blood hemoglobin, identify at least one feature in the PPG cycle representative of blood plasma, and provide the identified feature representative of blood hemoglobin and the feature representative of blood plasma to a predictive model adapted to identify a hemoglobin level as a function of the features.

The processor can be further programmed to calculate a ratio of the at least one feature in the PPG cycle representative of blood hemoglobin to the at least one feature in the PPG cycle representative of blood plasma, and provide the ratio to a predictive model adapted to identify a hemoglobin level as a function of the ratio.

The camera can be a red green blue (RGB) digital camera, and, for each of the first and second time series of images, the processor can further be programmed to subdivide each image into a plurality of blocks comprising a defined number of pixels, calculate a mean intensity value for the red pixels in each block, generate a time series signal identifying each image in the series versus an average value of a block for each of the first and second time series, and subsequently identify the at least one PPG signal in each of the first and second time series.

The predictive model can be stored in a remote computer having a second processor, and the operator transmits the videos to the remote computer. The predictive model can comprise a plurality of predictive models, each corresponding to a near infrared light selected to have a wavelength responsive to blood hemoglobin.

The lighting device can comprise a plurality of light emitting diodes mounted in an enclosure, wherein the enclosure includes a slot sized and dimensioned to receive a finger for illumination. The light emitting diodes can include at least one white light LED. The enclosure comprises a material selected to minimize interference from ambient light. The lighting device can comprises one or more coupling device for coupling the lighting device to a camera.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION

The present disclosure relates to the measurement of blood hemoglobin concentration using two optical absorption video sets of signals captured under near infrared light exposure with pulsatile blood volume changes. The blood volume changes are captured in the photoplethysmogram (PPG) signals generated. As described below, the measurement can be performed using a hand-held computing device such as a cell phone or smartphone. Images of dorsal fingertip tissue exposed to near infrared light wavelengths selected based on responsiveness to plasma and hemoglobin are acquired with simultaneous dorsal fingertip exposure to white light. The images can, for example, be obtained as a 10 second video of the ventral finger pad. The images allow creation two sets of photoplethysmogram (PPG) signal features that can be analyzed together to determine blood hemoglobin levels.

Photoplethysmogram

Figure 1:
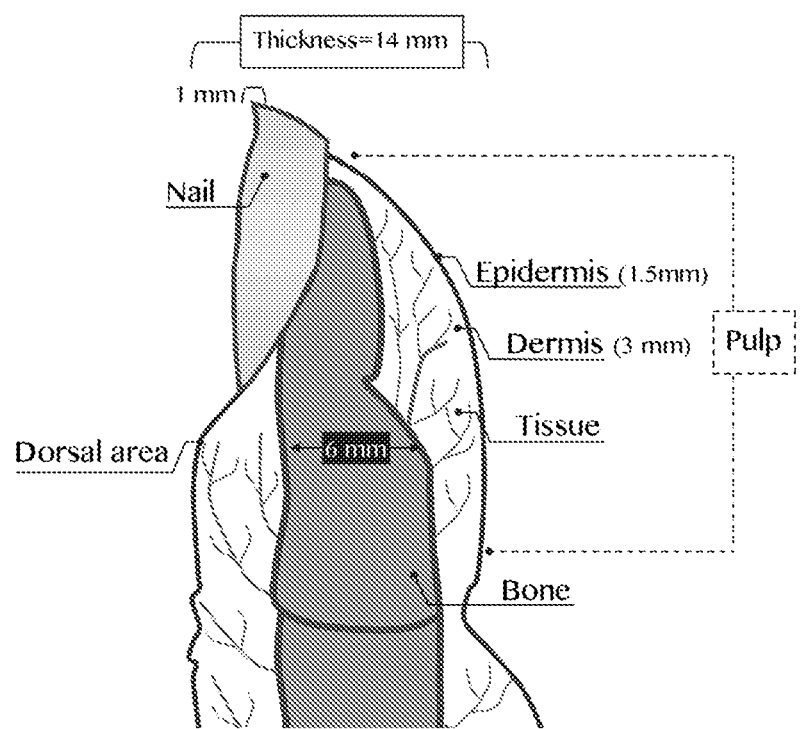
FIG. 1 illustrates a finger where its approximately 15 mm thickness is penetrated by near infra-red (NIR) light that is minimally absorbed by the intervening tissues, from the dorsal to the ventral surfaces. Through ballistic, snake and diffuse photon scattered paths, NIR light exposure on the dorsal side of the finger, despite intervening finger nail and osseous tissues, can be detected on the ventral surface.

PPG is an optical technique for observing blood volume changes noninvasively in the microvascular bed of tissue. Referring now to FIG. 1, a PPG system includes a light source and a photodetector where the light source illuminates the tissue area (e.g., a finger), and the photodetector captures the variation of light intensity. In IR or near-IR wavelengths, the changes in blood flow in tissues such as finger and muscle due to arteries and arterioles can be detected using PPG sensors. The PPG signal can be captured by detecting light intensity which is reflected or transmitted from the tissue. The intensity variations are observed due to vascular blood pressure changes. The PPG signal represents the differences in light intensities with the pulse.

A PPG waveform has two main components: a direct current (DC) component and an alternating current (AC) component. The direct current (DC) component is generated by the transmitted or reflected signal from the tissue and the average blood volume of both arterial and venous blood (see FIG. 4). The AC component fluctuates with the blood volume in the systolic and diastolic phases. When a finger is illuminated under two different wavelengths of NIR lights, and a ratio between the AC and DC components is determined for each, the effects from tissue and venous blood can be removed, providing a measure of the hemoglobin level.

To measure the hemoglobin level with respect to the blood plasma level, one response can be from the blood hemoglobin and another response from the blood plasma. In living tissue, water absorbs photons strongly above the 1000 nm wavelength of light; melanin absorbs in the 400 nm-650 nm spectrum. Hemoglobin response occurs across a spectrum from 650 to 950 nm. The spectrum range from 650 nm to 1100 nm is known as the tissue optical window or NIR region. To get a response from hemoglobin, an 850 nm wavelength NIR LED light which is hemoglobin responsive can be used. Similarly, to get a response from blood plasma, a 1070 nm wavelength NIR LED that is blood plasma responsive can be used. By analyzing the ratio of these two responses as presented as PPG signals, the tissue absorbance effects are removed and a more detailed characteristic of a PPG signal can be obtained for hemoglobin and plasma.

Figure 2:
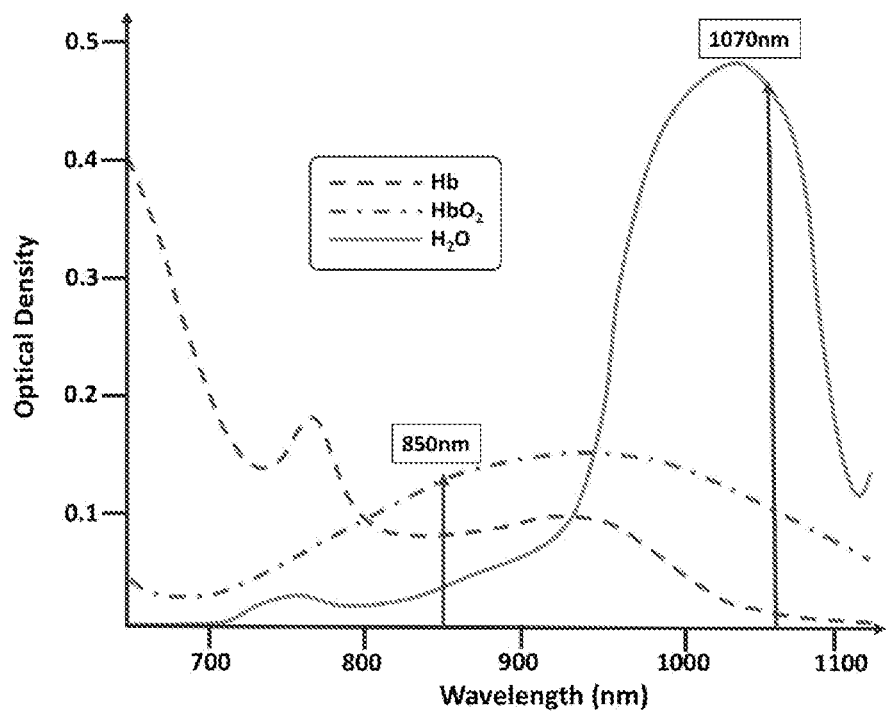
FIG. 2 illustrates the optical densities of the responses of oxygenated hemoglobin, deoxygenated hemoglobin, and plasma illuminated by light of various wavelengths.

Referring now to FIG. 2, in the finger, the blood, tissue, and bone absorb much of the non-IR (or visible range) light. A video camera can be used to capture the transmitted light, which changes based on the pulsation of arterial blood. The pulsation response can be extracted in time series data calculated from the fingertip video and converted into a PPG signal, which can be analyzed to build a hemoglobin prediction model. A small lighting surface can penetrate only a small part of the living tissue whereas a large planar lighting surface enables penetration of light to a deeper level (such as around bone tissue).

Acquire Image Data for a PPG Signal

Figure 3A:
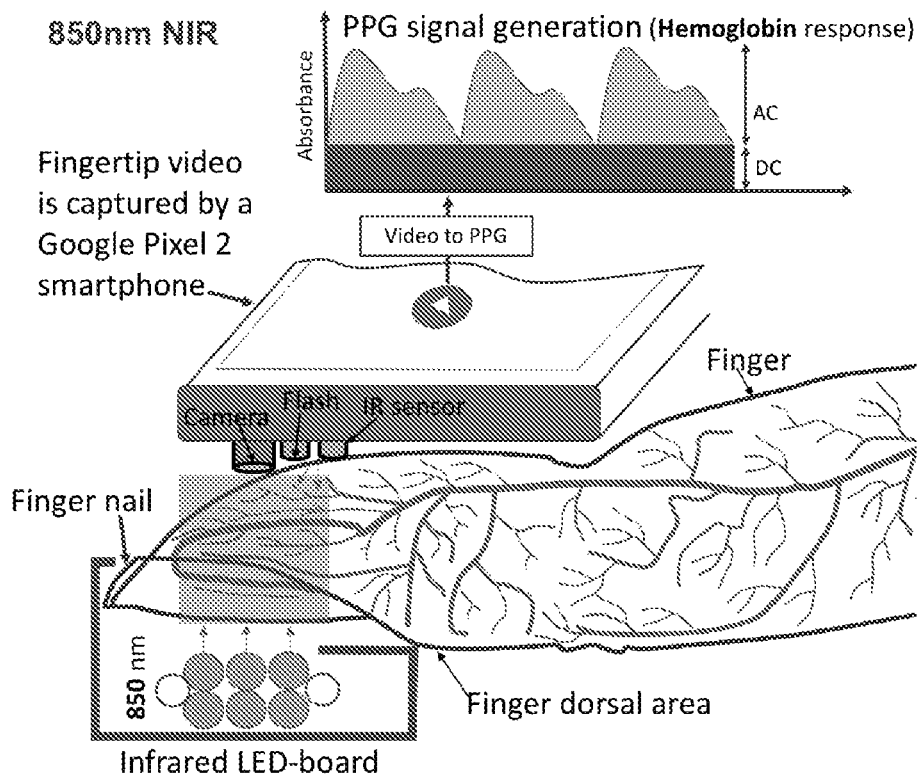
FIG. 3A illustrates the process of capturing a fingertip video using 850 nm NIR LED light board, and a plot of light intensity versus time (frame) where the graph defines a photoplethysmogram (PPG) signal caused by the modulation of light intensity by the changes in arterial blood volume change with each heartbeat.
Figure 3B:
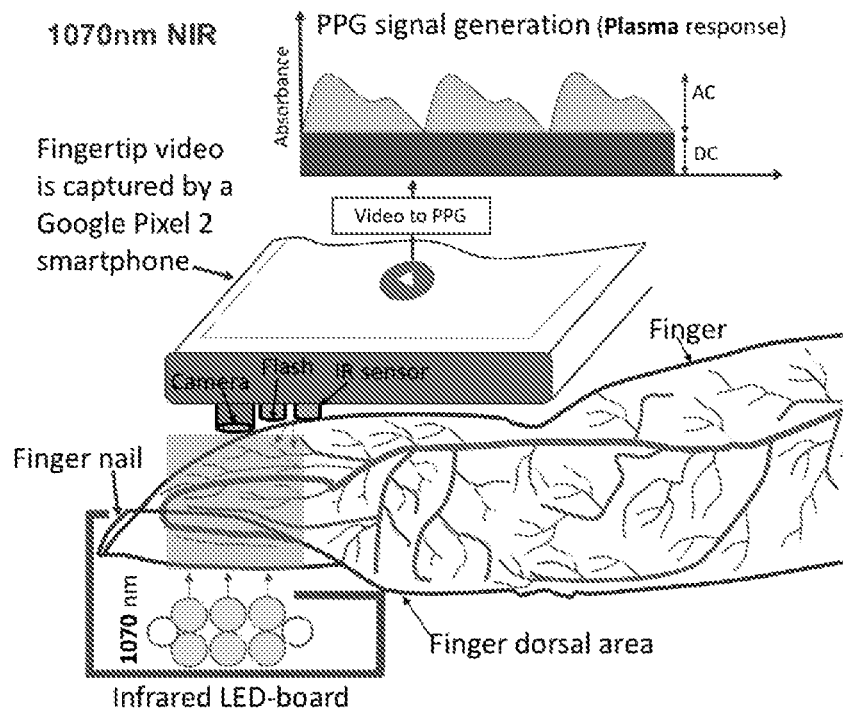
FIG. 3B illustrates the process of capturing a fingertip video using 1070 nm NIR LED light board, and a plot of light intensity versus time (frame) where the graph defines a PPG signal caused by the modulation of light intensity by the changes in arterial blood volume change with each heartbeat.

FIGS. 3A and 3B illustrate the approach for acquiring data. A finger, such as the index finger, is illuminated by two near-infrared (NIR) light sources with unequal wavelengths $\lambda_H$ and $\lambda_P$. The wavelength $\lambda_H$ is substantially sensitive to hemoglobin and insensitive to any other blood component. The light of wavelength $\lambda_P$ provides a significant response to blood plasma where other blood constituents have no response or negligible response under this NIR ($\lambda_P$) light. Here, 850 nm as $\lambda_H$ and 1070 nm as $\lambda_P$ NIR LED lights are used. To increase the amount of surface area that is illuminated, a number of LEDs of the same wavelength can be used. In our system, six 850 nm NIR and two white LED lights were used for the hemoglobin response (light source $L_{850}$, having a wavelength $\lambda_H$), and six 1070 nm NIR, and two LED white lights were used for the plasma response (light source $L_{1070}$, having wavelength $\lambda_P$). The NIR and white light are always turned on while collecting the data. The white light enables acquiring a photo of the finger that can be visualized.

Figure 4:
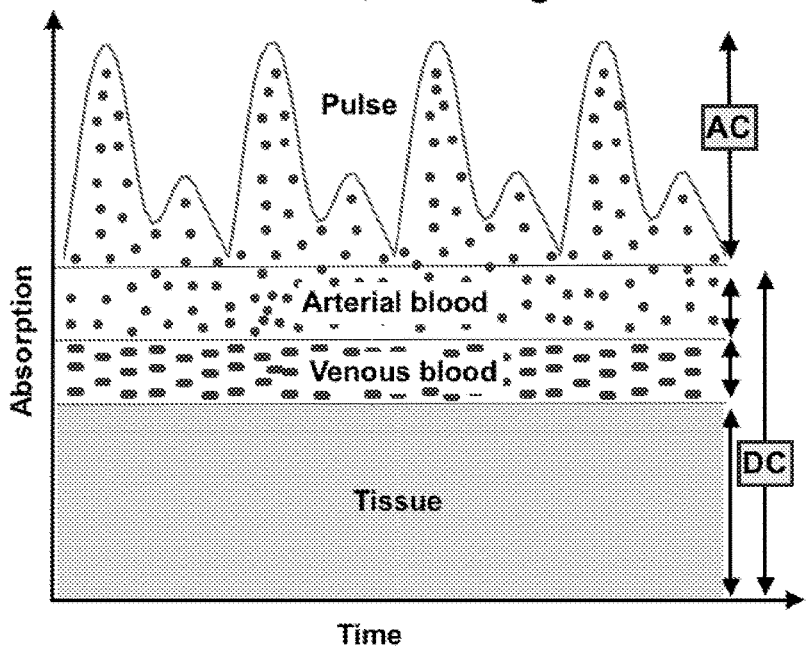
FIG. 4 illustrates a PPG signal generated from a fingertip video.
Figure 5:
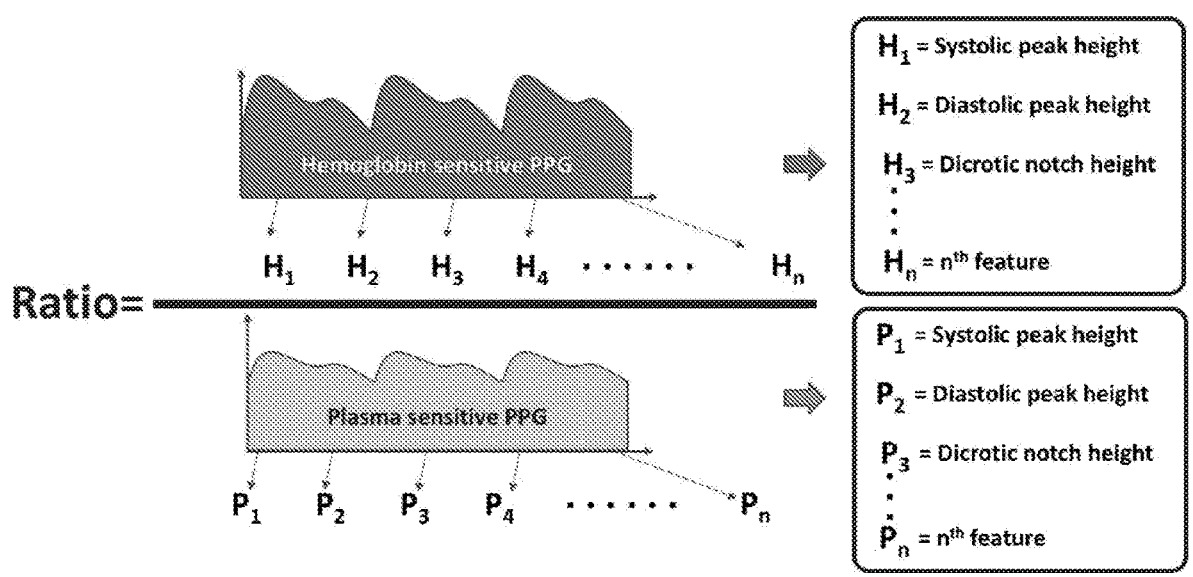
FIG. 5 illustrates the ratio of two PPG signals captured under two different wavelengths of NIR.

Referring still to FIGS. 3A and 3B, the light beams of both the L850 nm and L1070 nm light sources are applied to cross from the dorsal side of the finger to the pulp area, resulting in scattering and absorption in the tissue and bone. The light beams exit the ventral pad side of the finger by transmission and transflection and are captured by a video camera. By placing two different light sources $L_{850}$ and $L_{1070}$ under the dorsal side of a finger at different times, the response of hemoglobin and plasma can be captured in the fingertip videos, and these videos can then be converted to PPG signals. Here, one PPG signal is extracted from a video captured using light source $L_{850}$ and another PPG signal is generated using the fingertip video recorded under $L_{1070}$. Both PPG signals are presented in FIG. 3. A plot of the PPG intensity received for one light source over time or across the frame number is illustrated in FIG. 4. The relative magnitude of the AC signal is due to increased amount of blood (in systolic phase) and the decreasing amount of blood (in the diastolic phase). In addition to the AC component, there is a DC component that is steady in magnitude since this light intensity is captured in the tissue and non-pulsating venous blood. The value of each PPG signal captured for both light sources $L_{850}$ and $L_{1070}$ are normalized by dividing the AC component by the DC component. Here, the value calculated by—

$$AC_{850}/DC_{850}$$

is defined as $R_{850}$ and $$AC_{1070}/DC_{1070}$$

as $R_{1070}$. The normalized value of a PPG signal cancels out the effect of tissue, so that $R_{850}$ represents the hemoglobin response and $R_{1070}$ the plasma response. By calculating the ratio of $R_{850}$ and $R_{1070}$, a relationship is generated which provides the information on the light absorbed by both hemoglobin and plasma. The ratio of $R_{850}$ and $R_{1070}$ for each subjects' PPG signal in a mathematical model is then highly correlated with laboratory-measured ("gold standard") hemoglobin values as shown in FIG. 5. In addition to the ratio of AC and DC component of a PPG, other features from the PPG signal such as relative augmentation of a PPG, area under the systolic peak and diastolic peak, a slope of each peak, and a relative timestamp value of the peak, can be calculated or otherwise determined, as discussed below.

Pre-Process Data and Identify Region of Interest in Images

To identify a region of interest in the acquired video data, the following steps are taken:
1. Extract all frames from the video.
2. Subdivide each frame into blocks and assign an index number to each block. In one example, the frames were divided into 10×10 blocks, and the index numbers ranged from 1 to 100 where the number 1 starts from top left part of the frame increases towards the right (See FIG. 6).
3. Generate time series signal for each block from the starting frame to the last frame of the video
4. For each time series signal, perform the following steps:
   a. Apply bandpass filter to filter noise from the acquired video. In one example, a bandpass filter of 0.66 Hz-8.33 Hz was used, where the minimum cut off value was selected to discard the signal fluctuations due to breathing (0.2-0.3 Hz). The other sources of noise can include finger movements, finger quaking resulting in motion artifacts, coughing, and gasping.
   b. Sample using the Nyquist frequency as frames per second (FPS)/2. In one example, the frames per second is 60, and FPS/2 is 60/2=30.
   c. Filter the data to remove areas of fluctuation at the beginning and end due to finger movement to start and stop the video camera.
   d. Define this filtered and cropped signal as the PPG signal and look for three good PPG cycles where each cycle includes a systolic peak and a diastolic peak.
   e. If three continuous PPG cycles are not found, then select at least one cycle which has a systolic peak and a diastolic peak, replicate the selected cycle three times, and combined them to make a three-cycle PPG signal as shown in FIG. 7.
   f. Transfer this PPG signal with three cycles to extract the features.

Figure 6:
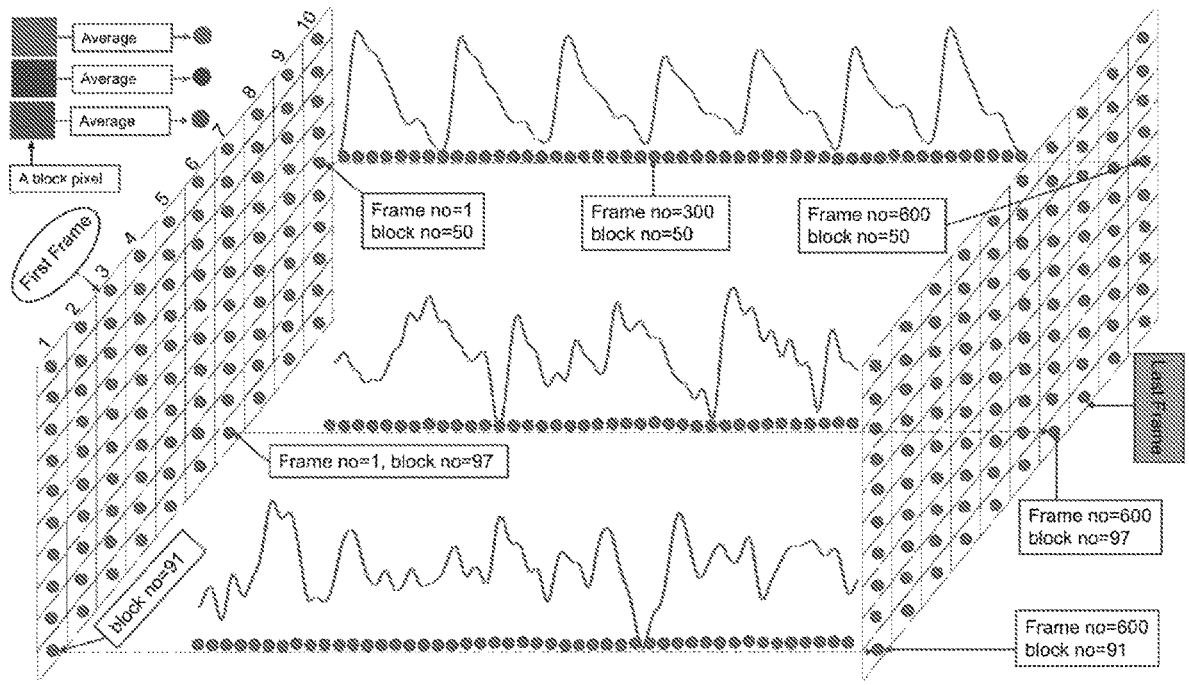
FIG. 6 illustrates the subdivision of an image frame to generate multiple time series signals.
Figure 7:
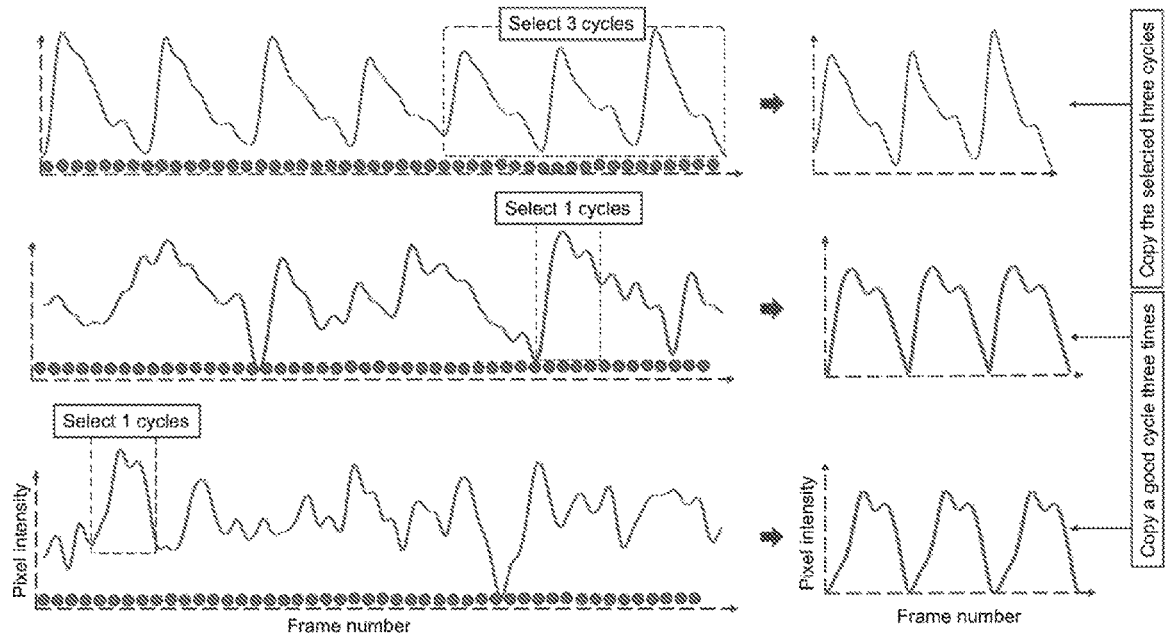
FIG. 7 illustrates PPG signal generation from a time series signal.

Referring now to FIG. 6, in one example, six 140 mW NIR LEDs were used, along with two white LED lights. These eight LED lights were put in one LED-board which was used for video recording. Three LED boards were created with three light wave-lengths: 850 nm, 940 nm, and 1070 nm NIR LED lights. Videos were acquired at a rate of 60 frames per second (FPS), by a camera that had a 1080×1920-pixel resolution. Here, in a 10-second video, there are 600 frames per 10 second video, and a single block of 10×10 block matrix contains 108×192 pixels of information.

Referring still to FIG. 6, each frame of the video has three two-dimensional pixel intensity arrays for each color: red, green, and blue (RGB). Since each frame has 10×10 blocks, a mean value is computed from each color pixel for each block of a frame which gives 100 mean values (dots in FIG. 6) for one frame. In FIG. 6, 600 frames extracted from a fingertip video are illustrated as subdivided into the 10×10 block matrix. Then, a time series signal is generated, with the frame number in the X-axis and the calculated averaged value of a block in Y-axis. FIG. 6 illustrates three different time series signals for red pixel intensity between first and last frame where the top signal was generated by block number 50, the middle signal was made by block number 97, and the third signal was calculated from block number 91. The dot in each block represents the average of all red pixel intensities of the block area. This dot is the averaged value of the all red pixels in the block. Since each dot has a different intensity, the plot of their averaged values across all frames produce a time series signal. Only red pixel intensities were used because only weak intensity signals were found with green and blue pixels.

After generating the PPG signal from the fingertip video, features were extracted from each PPG signal. Referring now to FIG. 7, three PPG cycles for each block of a video were captured. From these, the AC (systolic peak) and DC (trough) can be measured and used for hemoglobin level analysis.

Figure 8:
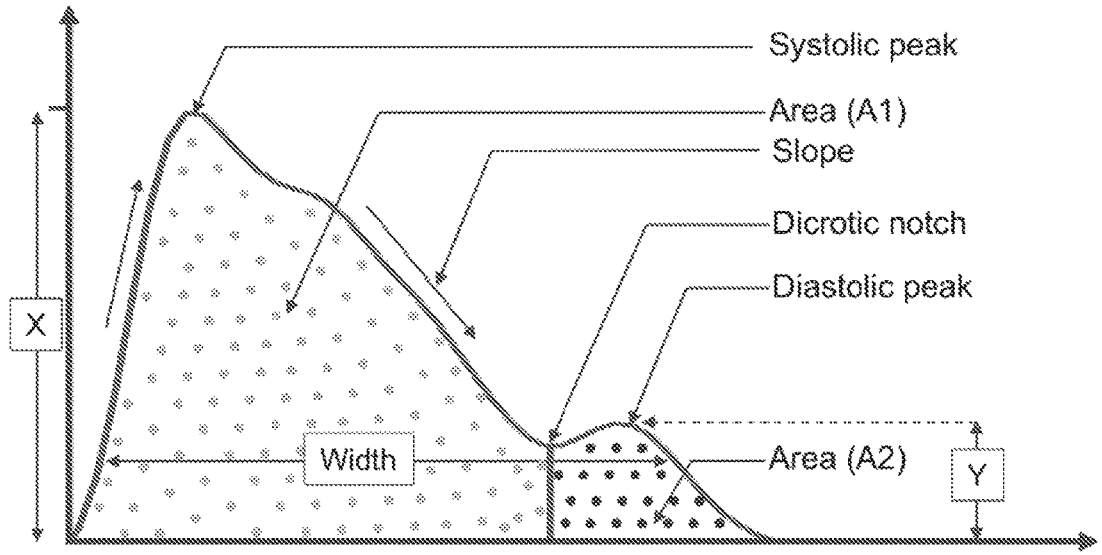
FIG. 8 illustrates multiple features of a PPG signal.
Figure 9:
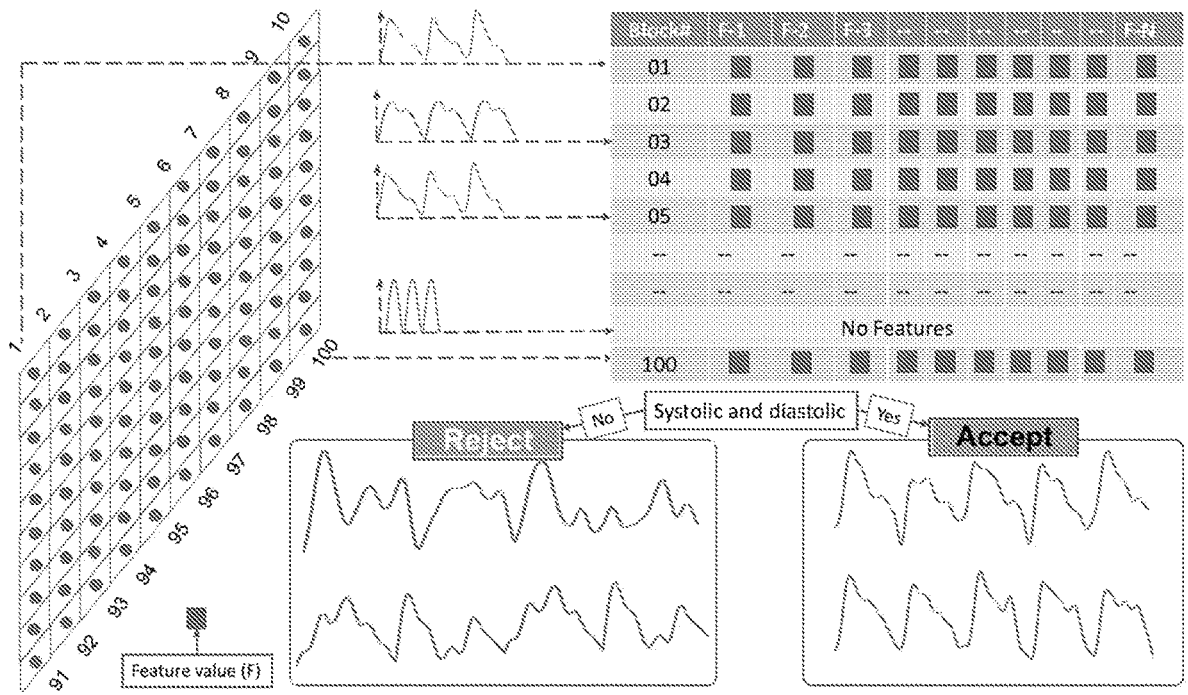
FIG. 9 illustrates feature generation from a PPG signal generated in all blocks.
Figure 10:
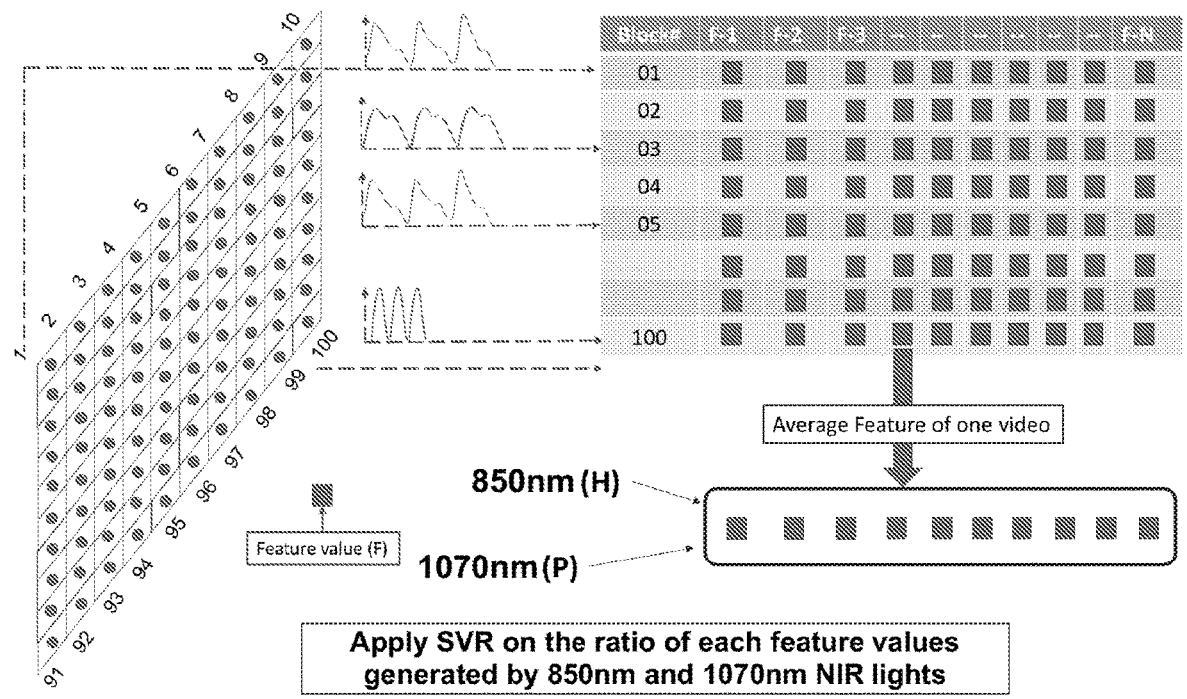
FIG. 10 illustrates features captured from 100 blocks averaged.

Referring now to FIG. 8, to characterize the PPG signal generated on each infrared (IR) LED light more fully, features including its diastolic peak, dicrotic notch height, ratio and augmented ratio among systolic, diastolic, and dicrotic notch, systolic and diastolic rising slope, and inflection point area ratio were extracted. About 80% of blocks that have a PPG include these features. The rest of the blocks are assigned as no feature values as shown in FIG. 9 and filtered out. To determine whether a specific PPG signal should be used, systolic and diastolic peaks are noted, and the height of the systolic peak is checked to verify that it is higher than the diastolic peak. If any block has no single PPG cycle that satisfies the selection criteria, the signal does not provide an adequate PPG, and the features are not determined. Finally, the PPG features calculated from a fingertip video are averaged (See FIG. 10).

Constructing the Model

To develop a hemoglobin prediction model, fingertip videos and corresponding known gold standard hemoglobin levels of 167 adult individuals were used; these data were selected from an initial set from 212 individuals. Forty-five cases exhibited poor quality video images or missing laboratory values, and were filtered out. Of the remaining 167 subjects, 82 were men and 85 were women. Laboratory hemoglobin levels ranged from 9.0-13.5 gm/dL across the set of subjects. Video data were acquired with the finger illuminated with three LED boards at 850 nm, 940 nm, and 1070 nm light wave lengths. The data were analyzed using the Support Vector Machine Regression (SVR), where SVR uses "Gaussian" kernels to build the prediction model using support vectors.

Figure 11:
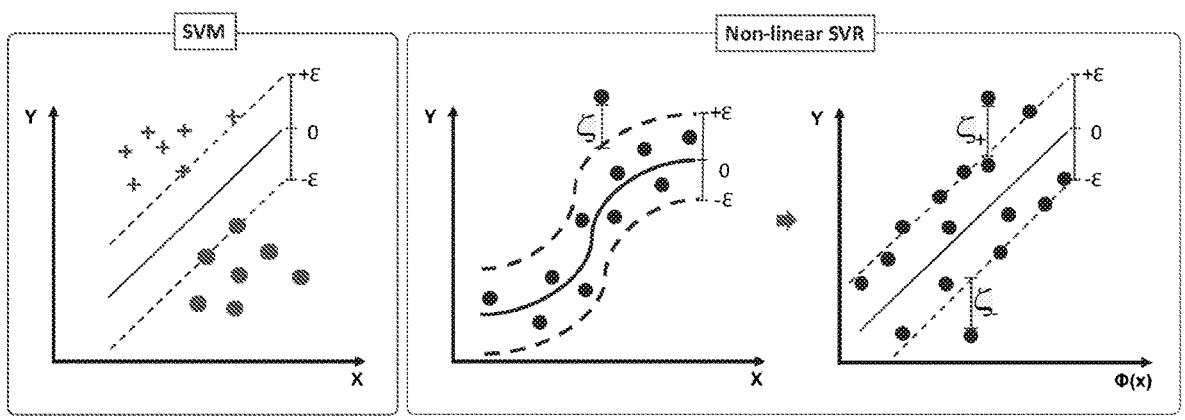
FIG. 11 illustrates the Support Vector Machine (SVM) algorithm for linear and non-linear regression.

The Support Vector Machine (SVM) maximizes the boundary value (sometimes called a "wide street") to generate a line that separates two classes, as illustrated in FIG. 11. In the regression, the model predicts a real number and optimizes the generalization bounds given for regression. Here, the loss function is known as the epsilon intensive loss function as shown in FIG. 11. In SVR, the input matrix is mapped onto multi-dimensional feature space applying non-linear mapping to build a linear model as shown in Equation 1 where $\varphi j(x)$, j=1, 2, 3, m is a set of non-linear transformations and 'b' is the 'bias' term.

$$f(x,\omega)=\Sigma_{j=1}^{m}\omega_{j}\varphi_{j}(x)+b \quad (1)$$

The SVR uses ε-intensive loss function.

$$\min \tfrac{1}{2}\|\omega\|^{2}+C\Sigma(\zeta_{+}+\zeta_{-}) \quad (2)$$

subject to $$\begin{cases} y_i - f(x_i, \omega) \le \in +\zeta_+ \\ f(x_i, \omega) - y_i \le \in +\zeta_- \\ \zeta_+, \zeta_- > 0, i = 1, 2, 3 \ldots, n \end{cases} \quad (3)$$

In the data analysis, MATLAB command "fitrsvm" was used with Xtrain, Ytrain, and "Gaussian" kernel as parameters. The "Standardize" function was set to standardize the data using the same mean and standard deviation in each data column. The prediction model was generated as a "Gaussian SVR Model" and the test data applied on this model using the MATLAB command "predict", while providing the model and test data as the parameter. The results are illustrated using MAPE, correlation coefficient (R), and Bland-Altman plot.

The Mean Absolute Percent Error (MAPE) is a commonly used metric to present the error level in the data. The MAPE is calculated as the following equation 4.

$$M = \frac{100\%}{1} \sum_{i=1}^{n} \frac{|A_t - E_t|}{|A_t|} \quad (4)$$

Where, $A_t$=Actual value or gold standard measurement, $E_t$=estimated value, and n=number of measurements or observations. MAPE has been used because MAPE does not depend on scale.

The correlation coefficient R can also be used to determine how strongly two measurement methods are related. R is computed as the ratio of covariance between the variables to the product of their standard deviations. The value of R is in between −1.0 and +1.0. If the value of R is +1.0 or −1.0, then a strong linear relationship between two estimation methods, and the linear regression can be calculated. The R value, however, does not identify whether there is a good agreement between the measurement methods. The Bland-Altman plot was used to evaluate a bias between the mean differences and to assess the agreement between the two measurement processes. The formula for Pearson's correlation is:

$$R = \frac{\sum_{i=1}^{n}(x_i - \bar{x})(y_i - \bar{y})}{\sqrt{\left[\sum_{i=1}^{n}(x_i - \bar{x})^2\right]\left[\sum_{i=1}^{n}(y_i - \bar{y})^2\right]}} \quad (5)$$

where, n is the sample size, $x_i$, $y_i$ are the individual sample points indexed with i,
$\bar{x}=\frac{1}{2}\Sigma_{i=1}^{n}x_i$ is the sample mean, and $\bar{y}=\frac{1}{2}\Sigma_{i=1}^{n}y_i$ is the target mean value.

The Bland-Altman graph plot represents the difference between the two measurement methods against the mean value of the measurement. The differences between these two methods are normally plotted against the mean of the two measurements. A plotting difference against mean helps identify the relationship between measurement error and the clinically measured value.

As described above, the model was developed using data from 167 subjects, which was filtered from an initial set of data of 212 fingertip videos. (IR) LED lights were applied with wavelengths of 850 nm, 940 nm, and 1070 nm. A Google Pixel 2 smartphone was used to capture video at 60 frames per second (FPS). The Google Pixel 2 has a 950 nm LED on board, and video was also acquired using this LED.

Sixteen PPG features were computed from a block of a video (600 frames) including systolic peak, diastolic peak, a dicrotic notch, augmentation among those peaks, peaks arrival time, inflection point area ratio, and peak rising slopes. To normalize the data, a ratio of two PPG features generated from different wavelengths of light was used. The ratio of two PPG signals' feature values was calculated as follows:

$$R_{1070}(850) = \frac{PPG_{850}}{PPG_{1070}} \quad (6)$$

The ratio of two PPG feature values here is the individual ratio between each feature value. For example, the ratio of the systolic peak value under a 1070 nm NIR light and the systolic peak value under an 850 nm NIR. Similarly, the ratio of all other features that were applied to the SVR machine learning algorithm were measured, along with ratios for the other wavelengths, referred to as herein as $R_{1070}(940)$, $R_{1070}(Pixel2)$ where:

$$R_{1070}(940) = \frac{PPG_{940}}{PPG_{1070}} \quad (7)$$

$$R_{1070}(Pixel2) = \frac{PPG_{Pixel2}}{PPG_{1070}} \quad (8)$$

Here, PPG1070 was considered as a plasma responsive PPG signal, as discussed above. The other PPG signals were chosen as hemoglobin responsive PPG signal.

Figures 12A, 12B:
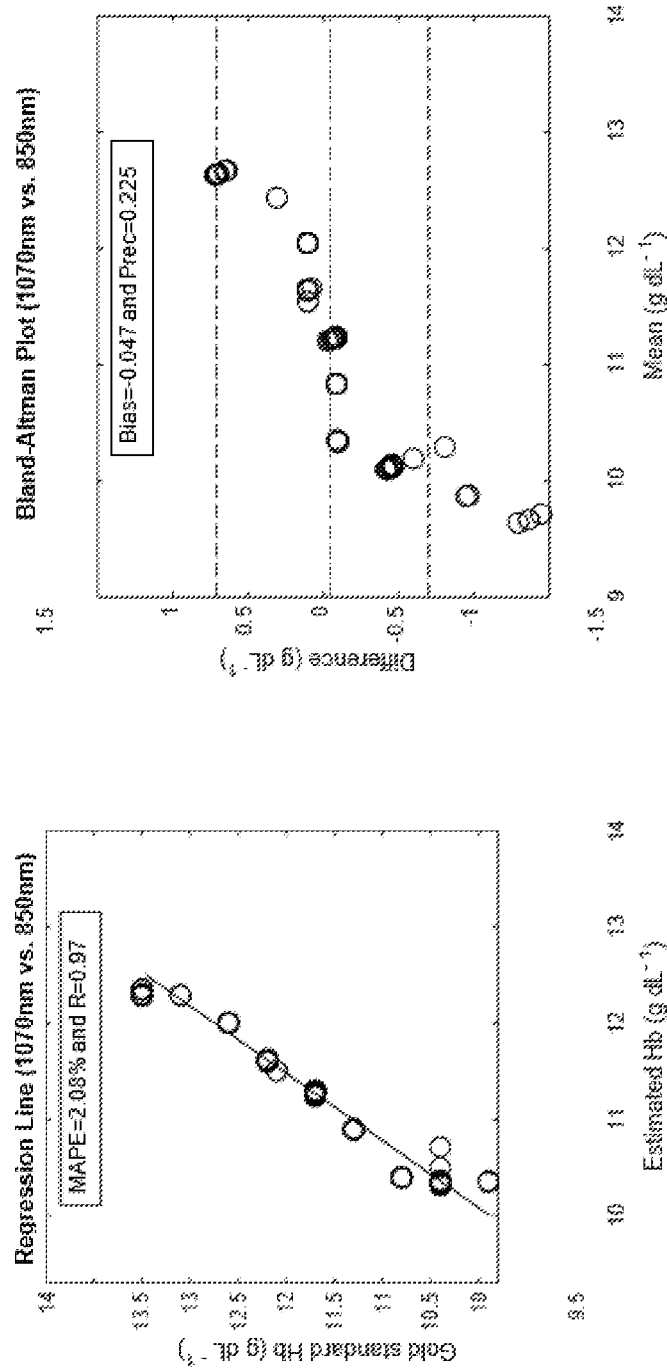
FIG. 12A illustrates the regression line developed based on gold standard-laboratory-measured hemoglobin levels and the estimated hemoglobin values using Model.
FIG. 12B illustrates the Bland-Altman plot for estimated hemoglobin levels using Model.

As described above, SVR was applied to the features generated from each of these ratios. For the ratio $R_{1070}(850)$ (Equation 6), an optimal prediction model was developed and defined. A regression line based on the clinically measured hemoglobin levels and the estimated hemoglobin values is illustrated in FIG. 12 based a combination of features that gave this optimal result. In FIG. 12a, the Mean Absolute Percentage Error (MAPE) is 2.08% where the linear correlation coefficient (R) between gold standard and estimated hemoglobin was 0.97.

Comparative Predictive Model Results

Other models using data obtained with the LED light board at 940 nm, and a cell phone camera using only the white light with this phone on the ventral finger pad were developed and evaluated. The described model was found to be the most accurate and predictive.

Hemoglobin Estimation Procedure Using the Predictive Model

With further confirmatory data, the predictive model described above can therefore be used to provide a noninvasive point of care tool for hemoglobin assessment. In this framework, a fingertip video is recorded while the finger is illuminated by two near-infrared (NIR) light sources with unequal wavelengths, one that is sensitive to hemoglobin ($\lambda_H$) and another that is sensitive to plasma ($\lambda_P$). The videos are then processed as described above and analyzed as in the defined optimal prediction model.

Figure 13:
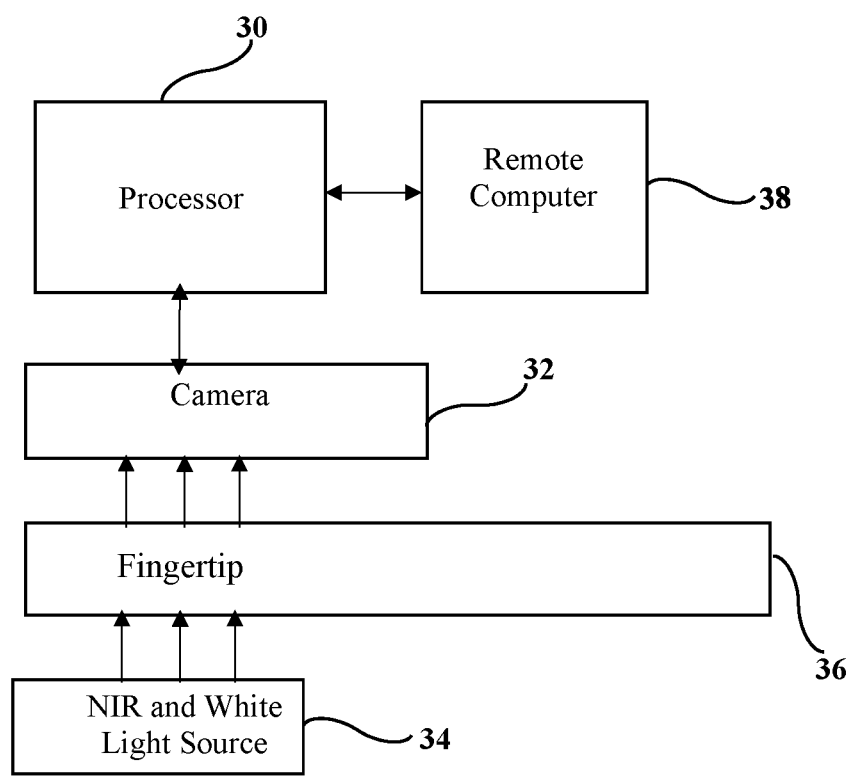
FIG. 13 is a block diagram of a system for performing a non-invasive hemoglobin level test in accordance with at least some embodiments of the current disclosure.

Referring now to FIG. 13, a block diagram of a device or system of devices for analyzing an object of interest, such as a finger, in accordance with the present disclosure is shown. The system includes a processor 30 which is in communication with a camera 32 and a light source 34. In operation the light source is activated, either by the processor or individually by, for example, input from a user or caregiver, and is positioned to shine light on the object of interest 36, which in the system described here is the finger 36. The camera 32 takes a series of pictures of the finger 36, which are preferably video but could, in some cases, be still photographs acquired in sufficiently quick succession to enable reproduction of a PPG signal, as described above. The image data is provided to the processor 30 which can either process the image data, as described below, or optionally transmit the data to a remote computer system 38 for analysis. The processor 30, camera 32, and light 34 can be part of a single device, which can be produced specifically for the application, but can also be a smart phone, laptop, tablet, or other devices having the described equipment and capable of providing light on an object to be evaluated and to acquire images of the object. The processor, camera, and light can all also be provided as separate components. The remote computer system 38 can, for example, be a cloud computer system or other types of wired or wireless networks. As described more fully below, the system can be used to evaluate hemoglobin by processing the frames of the image data and applying a trained machine learning model. Although not shown here, the processor can be further connected to various user interfaces, including a display, keyboard, mouse, touch screen, voice recognition system, or other similar devices.

In one example, image data can be captured using a personal electronic device containing processor 30, and camera 32, and the data transferred through a communications network to the remote computer or server 38 using secure communications for processing. For example, video images can be acquired with a smart phone, and a mobile application (app), such as an Android or iOS-based application, and sent to a cloud server 38 through the internet. A software application can be stored on the hand-held device and used to capture, for example, a 10-second fingertip video with the support of the built-in camera and a near infrared LED device adapted to provide illumination on a finger. The remote computer 38 can provide user authentication, video processing, and feature extraction from each video, as described above. Other methods of communicating to a remote computer can include, for example, communications via wired or wireless networks, cellular phone communications, Bluetooth communications, or storing data on a memory device and transferring the information to the remote computer through a memory drive or port.

A mobile application can store data useable by the camera 32 to monitor the position of the user's finger for appropriate placement, and activate an indicator, such as a light, or a speaker, to provide a signal to the user when the finger is appropriately positioned. The camera can also compare to stored data to evaluate whether the finger is sufficiently motionless to acquire data with the camera, and whether the finger is applying normal pressure. A video recording process can be automatically started by the mobile application when the user's finger is appropriately positioned so that user doesn't have to activate the video recording button, and stopped after a pre-determined period of time, such as a 10-second duration. The application can communicate with and automatically transfer video to the remote computer 38 or ask the user to affirm whether they are ready to transmit the data. Based on available bandwidth, the entire video can be transferred at one time. Alternatively, portions of the video can be iteratively sent to the remote computer 38. Communications through a USB port connection, Bluetooth, or other wired or wireless system can also be used with corresponding communications devices associated with the light device 34 to activate lighting.

Figure 14:
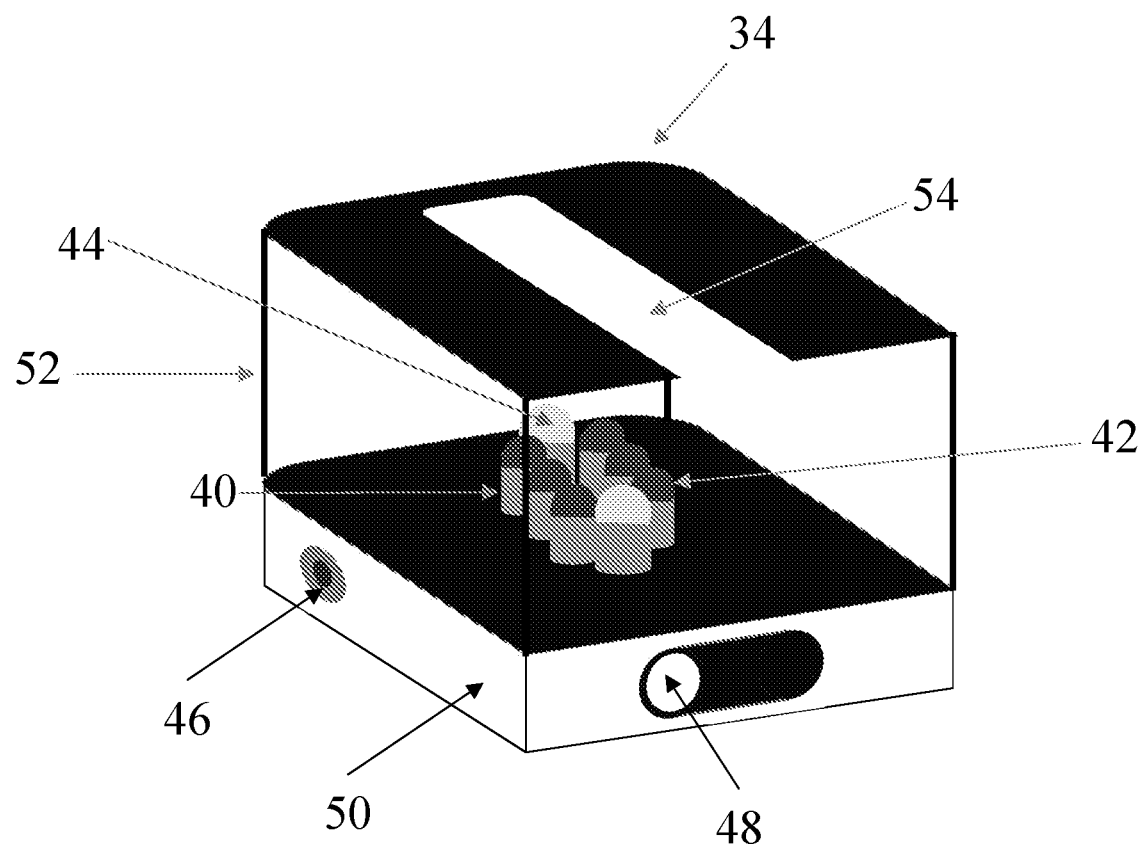
FIG. 14 is a schematic of a light source device constructed in accordance with the disclosure.

The light source 34 can be an LED associated with the device, and video can be acquired using the built-in camera in the equipment. In alternative embodiments, a specific NIR device, such as a printed circuit board can be provided (See, for example, FIGS. 3A and 3B). Referring now to FIG. 14, as discussed above, the light source 34 can have, for example, a plurality of LEDs 40 emitting light at a wavelength of 850 nm, and another plurality of LEDs 42 emitting light at a wavelength of 1070 nm. Other wavelength variations within the spectrum range of 650 nm to 1100 nm are also possible. For example, wavelengths responsive to hemoglobin can be used in a range between 800 and 950 nm. Wavelengths responsive to plasma can be in the range of 950 nm-1100 nm, with a peak response at around 1000 nm. In one embodiment, to provide a sufficient amount of light, 6 LEDs of 140 mW were used for each wavelength. One or more white lights 44 can also be provided on the board. A battery, such as a rechargeable battery, can be provided to power the LEDs. A charging point 46 for charging the battery can be included, along with a three-way or on/off switch 48. Although a single board is illustrated here, in some applications, the LEDS of specific wavelengths can be provided on two separate devices or boards, one adapted to provide NIR light responsive to plasma, and a second adapted to provide NIR light responsive to hemoglobin. In one embodiment, six 850 nm LEDs were used to provide light responsive to hemoglobin and six 1070 nm LEDs were used to provide light responsive to plasma. Two white LEDs were used to illuminate the finger during acquisition of images. This configuration was shown to be particularly successful in providing an accurate reading of hemoglobin. A similar configuration using 950 nm light also provided reasonably accurate results.

Referring still to FIG. 14, the LEDs 40, 42, and 44 are preferably mounted to a printed circuit board that can be provided in a housing 50. The charging point 46, switch 48, and battery can also be mounted in the housing 50. A light restrictive enclosure 52, which encloses the LEDs, is mounted to the housing 50, and comprises a slot 54 sized and dimensioned to receive a finger illuminated by the LEDs 40, 42, and 44. The shape of the upper layer of the enclosure 52 enables positioning a finger adjacent the board for illumination. In particular, the enclosure 52 is dimensioned to cause the dorsal area of the finger to touch the LEDs 40 and 42, and video can be captured from the opposing ventral side of the finger. Although the sides of the enclosure 52 are illustrated as open to enable viewing the LEDs, the sides of the enclosure are typically closed to prevent ambient illumination from interfering with the LEDs. The enclosure is preferably black in color, and can further be constructed of a material selected to minimize light interference from outside of the enclosure. Although a box shape is illustrated here, the shape of the enclosure is not limited to box-like enclosures, but can include, for example, a round or oblong profile sized to receive a finger, or other types of enclosures. Further, although three LEDs of each wavelength are illustrated here, the number of LEDs is not intended to be limiting. Various numbers of LEDs can be used. As described above, it has been shown experimentally that six or more LEDs of each wavelength provide improved results. Further, although LEDs of two different wavelengths are illustrated in the LED device here, LEDs 40 and 42 can be provided in separate LED devices. Where LEDs of both wavelengths are provided, the switch 48 can be a three way switch, switching between LEDs 42, LEDs 44, and an off position. When LEDs of one wavelength are provided in the enclosure, the switch 48 can be a two way on/off switch. In some applications, the LED device can be coupled to a camera, video camera, or a handheld device including a camera such as a smartphone, tablet, laptop, or similar device using brackets, straps, fasteners, adhesives, or other such devices.

Alternatively, the light 34 can be coupled directly to the user's finger, such as the index finger, using coupling devices including hook and loop fasteners, adhesives, tie straps, elastic bands, or similar elements. In some application, the light 34 device may be curved or otherwise formed specifically to engage a finger. The light 34 device may also include coupling elements enabling coupling of the device to a cellular phone or other device containing the processor 30 or to a camera 32.

The system can perform the hemoglobin level prediction at a local processor, such as the processor 30, or at a remote computer 38, which can be, for example, a cloud-based device. The cloud computing system can be HIPAA (Health Insurance Portability and Accountability Act) compliant or otherwise secured to address security and privacy issues, such as protected health information (PHI), to protect the stored database from unauthorized access, and data breach.

It should be understood that the methods and apparatuses described above are only exemplary and do not limit the scope of the invention, and that various modifications could be made by those skilled in the art that would fall under the scope of the invention. For example, although specific hardware configurations are described above, it will be apparent that a number of variations are available. Images of an illuminated finger could, for example, be acquired by a camera and transferred directly to a computer through hard wired or wireless links, or through transportable memory storage such as an SD card, USB flash drive, or other device. As described above, processing to analyze the hemoglobin content of a PPG signal acquired from a series of images or video can be performed by a local processor or computer, or at a remote location, such as a cloud device, as described above. Various off the shelf hand held devices, including smartphones and cellular phones that include an on-board camera and a processor can be used in the process described above. However, a device constructed specifically for this purpose can also be used.

To apprise the public of the scope of this invention, the following claims are made:

1. A system for non-invasive analysis of a hemoglobin level, the system comprising the following:
   a camera;
   a first lighting device comprising a near infrared light of a wavelength responsive to blood hemoglobin and adapted to illuminate a finger of a subject;
   a second lighting device comprising a near infrared light of a wavelength responsive to blood plasma and adapted to illuminate a finger of a subject;
   at least one processor, wherein the at least one processor is programmed to:
   receive a first time series of images of a ventral pad of the finger of a subject while illuminated by the first lighting device from a dorsal side of the finger, the first time series of images acquired by the camera under conditions selected to capture at least one complete detailed Photoplethysmography (PPG) cycle representative of blood hemoglobin; and
   receive a second time series of images of the ventral pad of the finger of the subject while illuminated by the second lighting device from a dorsal side of the finer, the second time series of images acquired by the camera under conditions to capture at least one complete detailed PPG cycle representative of plasma;
   identify at least one feature in the PPG cycle representative of blood hemoglobin;
   identify at least one feature in the PPG cycle representative of blood plasma;
   provide the identified feature representative of blood hemoglobin and the feature representative of blood plasma to a predictive model adapted to identify a hemoglobin level as a function of the features.

2. The system of claim 1, wherein the processor is further programmed to:
   calculate a ratio of the at least one feature in the PPG cycle representative of blood hemoglobin to the at least one feature in the PPG cycle representative of blood plasma; and
   provide the ratio to a predictive model adapted to identify a hemoglobin level as a function of the ratio.

3. The system of claim 1, wherein the predictive model is stored in a remote computer having a second processor, and the processor is further programmed to transmit data for analysis to the remote computer.

4. The system of claim 3, wherein the remote computer comprises a database storing model data for hand held computerized devices including data related to an on-board camera of the hand held computerized device.

5. The system of claim 1, wherein the predictive model comprises a plurality of predictive models, each corresponding to a near infrared light selected to have a wavelength responsive to blood hemoglobin.

6. The system of claim 1, wherein the lighting device comprises a plurality of light emitting diodes mounted in an enclosure, wherein the enclosure includes a slot sized and dimensioned to receive a finger for illumination.

7. The system of claim 6, wherein the light emitting diodes include at least one white light LED.

8. The system of claim 6, wherein the enclosure comprises a material selected to minimize interference from ambient light.

9. The system of claim 6, wherein the lighting device comprises one or more coupling device for coupling the lighting device to a camera.

10. The system of claim 1, wherein the camera and the processor are embedded in a hand held computerized device.

11. The system of claim 10, wherein the hand held computerized device comprises a cellular phone.

12. The system of claim 1, wherein the near infrared light responsive to blood hemoglobin has a wavelength of between 800 and 950 nm and the near infrared light responsive to plasma has a wavelength of 1070 nm.

13. The system of claim 12, wherein the near infrared light responsive to blood hemoglobin has a wavelength of 850 nm.

14. The system of claim 1, wherein the camera is a video camera.

15. The system of claim 1, wherein the camera is a red green blue (RGB) digital camera, and, for each of the first and second time series of images, the processor is further programmed to:
   subdivide each image in each of the first and second time-based series into a plurality of blocks comprising a defined number of pixels;
   calculate a mean intensity value for the red pixels in each block;
   generate a time series signal identifying each image in the series versus an average value of a block for each of the first and second time series; and subsequently identify the at least one PPG signal in each of the first and second time series.

16. The system of claim 1, wherein the processor is further programmed to calculate a ratio of the PPG signal of the first time-based series of images of a blood flow illuminated with a near infrared light responsive to blood hemoglobin, to the second time-based series of the images of a blood flow illuminated with a near infrared light responsive to blood plasma.

17. The system of claim 1, wherein the processor is further programmed to identify at least one feature in each of the PPG cycles to determine the hemoglobin level, wherein the feature comprises at least one of a relative augmentation of a PPG, an area under the systolic peak; an area under a diastolic peak, a slope of the systolic peak, a slope of the diastolic peak, a relative timestamp value of the peak, a normalized PPG rise time, a pulse transit time (PTT), a pulse shape, or an amplitude.

18. The system of claim 1, wherein processor is further programmed to:
- subdivide each image into a plurality of blocks comprising a defined number of pixels;
- calculate a mean intensity value for the red pixels in each block;
- generating a time series signal identifying each image in the series versus an average value of a block; and subsequently identify at least one PPG signal in each time series.

19. The system of claim 18, wherein the processor is further programmed to filter the data in each of the frames to identify the at least one PPG signal.

\* \* \* \* \*